United States Patent
Rafii-Tari et al.

(10) Patent No.: US 12,053,144 B2
(45) Date of Patent: *Aug. 6, 2024

(54) ROBOTIC SYSTEMS FOR NAVIGATION OF LUMINAL NETWORKS THAT COMPENSATE FOR PHYSIOLOGICAL NOISE

(71) Applicant: Auris Health, Inc., Redwood City, CA (US)

(72) Inventors: Hedyeh Rafii-Tari, Mountain View, CA (US); Ritwik Ummalaneni, San Mateo, CA (US); Chauncey F. Graetzel, Palo Alto, CA (US)

(73) Assignee: Auris Health, Inc., Redwood City, CA (US)

( * ) Notice: Subject to any disclaimer, the term of this patent is extended or adjusted under 35 U.S.C. 154(b) by 48 days.

This patent is subject to a terminal disclaimer.

(21) Appl. No.: 17/978,702

(22) Filed: Nov. 1, 2022

(65) Prior Publication Data

US 2023/0057983 A1    Feb. 23, 2023

Related U.S. Application Data

(63) Continuation of application No. 15/939,678, filed on Mar. 29, 2018, now Pat. No. 11,490,782.

(Continued)

(51) Int. Cl.
*A61B 1/00* (2006.01)
*A61B 1/267* (2006.01)
(Continued)

(52) U.S. Cl.
CPC ........ *A61B 1/00006* (2013.01); *A61B 1/2676* (2013.01); *A61B 5/062* (2013.01);
(Continued)

(58) Field of Classification Search
CPC ... A61B 1/00006; A61B 1/2676; A61B 5/062; A61B 5/0816; A61B 5/6867;
(Continued)

(56) References Cited

U.S. PATENT DOCUMENTS

| 1,063,914 A | 6/1913 | Dehlin |
|---|---|---|
| 4,745,908 A | 5/1988 | Wardle |

(Continued)

FOREIGN PATENT DOCUMENTS

| CN | 101147676 A | 3/2008 |
|---|---|---|
| CN | 101222882 A | 7/2008 |

(Continued)

OTHER PUBLICATIONS

Office action for U.S. Appl. No. 15/939,678, dated Jun. 29, 2020, 14 pages.

(Continued)

*Primary Examiner* — Hien N Nguyen
(74) *Attorney, Agent, or Firm* — Chang & Hale LLP

(57) ABSTRACT

Certain aspects relate to systems and techniques for luminal network navigation. Some aspects relate to incorporating respiratory frequency and/or magnitude into a navigation system to implement patient safety measures. Some aspects relate to identifying, and compensating for, motion caused by patient respiration in order to provide a more accurate identification of the position of an instrument within a luminal network.

20 Claims, 11 Drawing Sheets

Related U.S. Application Data

(60) Provisional application No. 62/480,257, filed on Mar. 31, 2017.

(51) Int. Cl.

| | | |
|---|---|---|
| *A61B 5/00* | (2006.01) | |
| *A61B 5/06* | (2006.01) | |
| *A61B 5/08* | (2006.01) | |
| *A61B 10/04* | (2006.01) | |
| *A61B 17/00* | (2006.01) | |
| *A61B 34/00* | (2016.01) | |
| *A61B 34/20* | (2016.01) | |
| *A61B 34/30* | (2016.01) | |
| *A61B 34/32* | (2016.01) | |
| *A61B 34/35* | (2016.01) | |
| *G06T 19/00* | (2011.01) | |
| *G16H 20/40* | (2018.01) | |
| *G16H 40/63* | (2018.01) | |
| *G16H 50/50* | (2018.01) | |

(52) U.S. Cl.
CPC .......... *A61B 5/0816* (2013.01); *A61B 5/6867* (2013.01); *A61B 10/04* (2013.01); *A61B 34/20* (2016.02); *A61B 34/30* (2016.02); *A61B 34/32* (2016.02); *A61B 34/35* (2016.02); *A61B 34/76* (2016.02); *G16H 40/63* (2018.01); *A61B 5/08* (2013.01); *A61B 5/7207* (2013.01); *A61B 5/7275* (2013.01); *A61B 5/7289* (2013.01); *A61B 2017/00699* (2013.01); *A61B 2034/2051* (2016.02); *A61B 2034/301* (2016.02); *A61B 2034/303* (2016.02); *G06T 19/003* (2013.01); *G06T 2200/24* (2013.01); *G06T 2210/41* (2013.01); *G16H 20/40* (2018.01); *G16H 50/50* (2018.01)

(58) Field of Classification Search
CPC ......... A61B 10/04; A61B 34/20; A61B 34/30; A61B 34/32; A61B 34/35; A61B 34/76; A61B 5/08; A61B 5/7207; A61B 5/7275; A61B 5/7289; A61B 2017/00699; A61B 2034/2051; A61B 2034/301; A61B 2034/303; A61B 2017/00809; A61B 2034/105; A61B 2034/2048; A61B 2034/2063; A61B 2090/3614; A61B 2090/371; A61B 34/10; A61B 2017/00123; G16H 40/63; G16H 20/40; G16H 50/50; G06T 19/003; G06T 2200/24; G06T 2210/41

See application file for complete search history.

(56) References Cited

U.S. PATENT DOCUMENTS

| | | | |
|---|---|---|---|
| 5,273,025 | A | 12/1993 | Sakiyama et al. |
| 5,526,812 | A | 6/1996 | Dumoulin et al. |
| 5,550,953 | A | 8/1996 | Seraji |
| 5,831,614 | A | 11/1998 | Tognazzini et al. |
| 5,935,075 | A | 8/1999 | Casscells et al. |
| 6,038,467 | A | 3/2000 | Bliek et al. |
| 6,047,080 | A | 4/2000 | Chen et al. |
| 6,059,718 | A | 5/2000 | Taniguchi et al. |
| 6,063,095 | A | 5/2000 | Wang et al. |
| 6,167,292 | A | 12/2000 | Badano et al. |
| 6,203,493 | B1 | 3/2001 | Ben-Haim |
| 6,246,784 | B1 | 6/2001 | Summers et al. |
| 6,246,898 | B1 | 6/2001 | Vesely et al. |
| 6,332,089 | B1 | 12/2001 | Acker et al. |
| 6,425,865 | B1 | 7/2002 | Salcudean et al. |
| 6,454,776 | B1 | 9/2002 | Tajima et al. |
| 6,466,198 | B1 | 10/2002 | Feinstein |
| 6,490,467 | B1 | 12/2002 | Bucholz et al. |
| 6,553,251 | B1 | 4/2003 | Lähdesmäki |
| 6,665,554 | B1 | 12/2003 | Charles et al. |
| 6,690,963 | B2 | 2/2004 | Ben-Haim et al. |
| 6,690,964 | B2 | 2/2004 | Bieger et al. |
| 6,755,797 | B1 | 6/2004 | Stouffer |
| 6,812,842 | B2 | 11/2004 | Dimmer |
| 6,899,672 | B2 | 5/2005 | Chin et al. |
| 6,926,709 | B2 | 8/2005 | Bieger et al. |
| 7,180,976 | B2 | 2/2007 | Wink et al. |
| 7,206,627 | B2 | 4/2007 | Abovitz et al. |
| 7,233,820 | B2 | 6/2007 | Gilboa |
| 7,386,339 | B2 | 6/2008 | Strommer et al. |
| 7,697,972 | B2 | 4/2010 | Verard et al. |
| 7,756,563 | B2 | 7/2010 | Higgins et al. |
| 7,850,642 | B2 | 12/2010 | Moll et al. |
| 7,901,348 | B2 | 3/2011 | Soper et al. |
| 8,155,403 | B2 | 4/2012 | Tschirren et al. |
| 8,190,238 | B2 | 5/2012 | Moll et al. |
| 8,290,571 | B2 | 10/2012 | Younge et al. |
| 8,298,135 | B2 | 10/2012 | Ito et al. |
| 8,317,746 | B2 | 11/2012 | Sewell et al. |
| 8,394,054 | B2 | 3/2013 | Wallace et al. |
| 8,460,236 | B2 | 6/2013 | Roelle et al. |
| 8,821,376 | B2 | 9/2014 | Tolkowsky |
| 8,858,424 | B2 | 10/2014 | Hasegawa et al. |
| 8,929,631 | B2 | 1/2015 | Pfister et al. |
| 9,014,851 | B2 | 4/2015 | Wong et al. |
| 9,084,623 | B2 | 7/2015 | Gomez et al. |
| 9,125,639 | B2 | 9/2015 | Mathis et al. |
| 9,138,129 | B2 | 9/2015 | Diolaiti |
| 9,183,354 | B2 | 11/2015 | Baker et al. |
| 9,186,046 | B2 | 11/2015 | Ramamurthy et al. |
| 9,272,416 | B2 | 3/2016 | Hourtash et al. |
| 9,289,578 | B2 | 3/2016 | Walker et al. |
| 9,459,087 | B2 | 10/2016 | Dunbar et al. |
| 9,504,604 | B2 | 11/2016 | Alvarez |
| 9,561,083 | B2 | 2/2017 | Yu et al. |
| 9,603,668 | B2 | 3/2017 | Weingarten et al. |
| 9,622,827 | B2 | 4/2017 | Yu et al. |
| 9,629,682 | B2 | 4/2017 | Wallace et al. |
| 9,636,184 | B2 | 5/2017 | Lee et al. |
| 9,710,921 | B2 | 7/2017 | Wong et al. |
| 9,713,509 | B2 | 7/2017 | Schuh et al. |
| 9,717,563 | B2 | 8/2017 | Tognaccini et al. |
| 9,727,963 | B2 | 8/2017 | Mintz et al. |
| 9,737,371 | B2 | 8/2017 | Romo et al. |
| 9,737,373 | B2 | 8/2017 | Schuh |
| 9,744,335 | B2 | 8/2017 | Jiang |
| 9,763,741 | B2 | 9/2017 | Alvarez et al. |
| 9,788,910 | B2 | 10/2017 | Schuh |
| 9,818,681 | B2 | 11/2017 | Machida et al. |
| 9,844,412 | B2 | 12/2017 | Bogusky et al. |
| 9,867,635 | B2 | 1/2018 | Alvarez et al. |
| 9,918,681 | B2 | 3/2018 | Wallace et al. |
| 9,931,025 | B1 | 4/2018 | Graetzel et al. |
| 9,949,749 | B2 | 4/2018 | Noonan et al. |
| 9,955,986 | B2 | 5/2018 | Shah |
| 9,962,228 | B2 | 5/2018 | Schuh et al. |
| 9,980,785 | B2 | 5/2018 | Schuh |
| 9,993,313 | B2 | 6/2018 | Schuh et al. |
| 10,016,900 | B1 | 7/2018 | Meyer et al. |
| 10,022,192 | B1 | 7/2018 | Ummalaneni |
| 10,046,140 | B2 | 8/2018 | Kokish et al. |
| 10,080,576 | B2 | 9/2018 | Romo et al. |
| 10,123,755 | B2 | 11/2018 | Walker et al. |
| 10,130,345 | B2 | 11/2018 | Wong et al. |
| 10,136,950 | B2 | 11/2018 | Schoenefeld |
| 10,136,959 | B2 | 11/2018 | Mintz et al. |
| 10,143,360 | B2 | 12/2018 | Roelle et al. |
| 10,143,526 | B2 | 12/2018 | Walker et al. |
| 10,145,747 | B1 | 12/2018 | Lin et al. |
| 10,149,720 | B2 | 12/2018 | Romo |
| 10,159,532 | B1 | 12/2018 | Ummalaneni |
| 10,159,533 | B2 | 12/2018 | Moll et al. |
| 10,169,875 | B2 | 1/2019 | Mintz et al. |
| 10,219,874 | B2 | 3/2019 | Yu et al. |
| 10,231,793 | B2 | 3/2019 | Romo |

(56) References Cited

U.S. PATENT DOCUMENTS

| | | |
|---|---|---|
| 10,231,867 B2 | 3/2019 | Alvarez et al. |
| 10,244,926 B2 | 4/2019 | Noonan et al. |
| 10,278,778 B2 | 5/2019 | State et al. |
| 10,285,574 B2 | 5/2019 | Landey et al. |
| 10,299,870 B2 | 5/2019 | Connolly et al. |
| 10,524,866 B2 | 1/2020 | Srinivasan et al. |
| 10,639,114 B2 | 5/2020 | Schuh et al. |
| 10,667,875 B2 | 6/2020 | DeFonzo et al. |
| 10,743,751 B2 | 8/2020 | Landey et al. |
| 10,751,140 B2 | 8/2020 | Wallace et al. |
| 10,765,487 B2 | 9/2020 | Ho et al. |
| 10,779,898 B2 | 9/2020 | Hill et al. |
| 10,814,101 B2 | 10/2020 | Jiang |
| 10,820,947 B2 | 11/2020 | Julian |
| 10,820,954 B2 | 11/2020 | Marsot et al. |
| 10,827,913 B2 | 11/2020 | Ummalaneni et al. |
| 10,828,118 B2 | 11/2020 | Schuh et al. |
| 10,973,422 B2 | 4/2021 | Pantelopoulos et al. |
| 11,490,782 B2 | 11/2022 | Rafii-Tari |
| 11,503,986 B2 | 11/2022 | Ye et al. |
| 2001/0021843 A1 | 9/2001 | Bosselmann et al. |
| 2001/0039421 A1 | 11/2001 | Heilbrun et al. |
| 2002/0065455 A1 | 5/2002 | Ben-Haim et al. |
| 2002/0077533 A1 | 6/2002 | Bieger et al. |
| 2002/0120188 A1 | 8/2002 | Brock et al. |
| 2003/0105603 A1 | 6/2003 | Hardesty |
| 2003/0125622 A1 | 7/2003 | Schweikard et al. |
| 2003/0181809 A1 | 9/2003 | Hall et al. |
| 2003/0195664 A1 | 10/2003 | Nowlin et al. |
| 2004/0047044 A1 | 3/2004 | Dalton |
| 2004/0072066 A1 | 4/2004 | Cho et al. |
| 2004/0097806 A1 | 5/2004 | Hunter et al. |
| 2004/0186349 A1 | 9/2004 | Ewers et al. |
| 2004/0249267 A1 | 12/2004 | Gilboa |
| 2004/0263535 A1 | 12/2004 | Birkenbach et al. |
| 2005/0027397 A1 | 2/2005 | Niemeyer |
| 2005/0060006 A1 | 3/2005 | Pflueger et al. |
| 2005/0085714 A1 | 4/2005 | Foley et al. |
| 2005/0107679 A1 | 5/2005 | Geiger et al. |
| 2005/0143649 A1 | 6/2005 | Minai et al. |
| 2005/0143655 A1 | 6/2005 | Satoh |
| 2005/0182295 A1 | 8/2005 | Soper et al. |
| 2005/0182319 A1 | 8/2005 | Glossop |
| 2005/0193451 A1 | 9/2005 | Quistgaard et al. |
| 2005/0197557 A1 | 9/2005 | Strommer et al. |
| 2005/0256398 A1 | 11/2005 | Hastings et al. |
| 2005/0272975 A1 | 12/2005 | McWeeney et al. |
| 2006/0004286 A1 | 1/2006 | Chang et al. |
| 2006/0015096 A1 | 1/2006 | Hauck et al. |
| 2006/0025668 A1 | 2/2006 | Peterson et al. |
| 2006/0058643 A1 | 3/2006 | Florent et al. |
| 2006/0084860 A1 | 4/2006 | Geiger et al. |
| 2006/0095066 A1 | 5/2006 | Chang et al. |
| 2006/0098851 A1 | 5/2006 | Shoham et al. |
| 2006/0149134 A1 | 7/2006 | Soper et al. |
| 2006/0173290 A1 | 8/2006 | Lavallee et al. |
| 2006/0184016 A1 | 8/2006 | Glossop |
| 2006/0209019 A1 | 9/2006 | Hu |
| 2006/0258935 A1 | 11/2006 | Pile-Spellman et al. |
| 2006/0258938 A1 | 11/2006 | Hoffman et al. |
| 2007/0032826 A1 | 2/2007 | Schwartz |
| 2007/0055128 A1 | 3/2007 | Glossop |
| 2007/0055144 A1 | 3/2007 | Neustadter et al. |
| 2007/0073136 A1 | 3/2007 | Metzger |
| 2007/0083193 A1 | 4/2007 | Werneth et al. |
| 2007/0123748 A1 | 5/2007 | Meglan |
| 2007/0135886 A1 | 6/2007 | Maschke |
| 2007/0156019 A1 | 7/2007 | Larkin et al. |
| 2007/0161857 A1 | 7/2007 | Durant et al. |
| 2007/0167743 A1 | 7/2007 | Honda et al. |
| 2007/0167801 A1 | 7/2007 | Webler et al. |
| 2007/0208252 A1 | 9/2007 | Makower |
| 2007/0253599 A1 | 11/2007 | White et al. |
| 2007/0269001 A1 | 11/2007 | Maschke |
| 2007/0293721 A1 | 12/2007 | Gilboa |
| 2007/0299353 A1 | 12/2007 | Harlev et al. |
| 2008/0071140 A1 | 3/2008 | Gattani et al. |
| 2008/0079421 A1 | 4/2008 | Jensen |
| 2008/0103389 A1 | 5/2008 | Begelman et al. |
| 2008/0118118 A1 | 5/2008 | Berger |
| 2008/0118135 A1 | 5/2008 | Averbuch et al. |
| 2008/0123921 A1 | 5/2008 | Gielen et al. |
| 2008/0147089 A1 | 6/2008 | Loh et al. |
| 2008/0161681 A1 | 7/2008 | Hauck |
| 2008/0183064 A1 | 7/2008 | Chandonnet et al. |
| 2008/0183068 A1 | 7/2008 | Carls et al. |
| 2008/0183073 A1 | 7/2008 | Higgins et al. |
| 2008/0183188 A1 | 7/2008 | Carls et al. |
| 2008/0201016 A1 | 8/2008 | Finlay |
| 2008/0207997 A1 | 8/2008 | Higgins et al. |
| 2008/0212082 A1 | 9/2008 | Froggatt et al. |
| 2008/0218770 A1 | 9/2008 | Moll et al. |
| 2008/0243142 A1 | 10/2008 | Gildenberg |
| 2008/0262297 A1 | 10/2008 | Gilboa et al. |
| 2008/0275349 A1 | 11/2008 | Halperin et al. |
| 2008/0287963 A1 | 11/2008 | Rogers et al. |
| 2008/0300478 A1 | 12/2008 | Zuhars et al. |
| 2008/0306490 A1 | 12/2008 | Lakin et al. |
| 2008/0312501 A1 | 12/2008 | Hasegawa et al. |
| 2009/0030307 A1 | 1/2009 | Govari et al. |
| 2009/0054729 A1 | 2/2009 | Mori et al. |
| 2009/0076476 A1 | 3/2009 | Barbagli et al. |
| 2009/0149867 A1 | 6/2009 | Glozman et al. |
| 2009/0209817 A1 | 8/2009 | Averbuch |
| 2009/0227861 A1 | 9/2009 | Ganatra et al. |
| 2009/0228020 A1 | 9/2009 | Wallace et al. |
| 2009/0248036 A1 | 10/2009 | Hoffman et al. |
| 2009/0259230 A1 | 10/2009 | Khadem et al. |
| 2009/0262109 A1 | 10/2009 | Markowitz et al. |
| 2009/0292166 A1 | 11/2009 | Ito et al. |
| 2009/0295797 A1 | 12/2009 | Sakaguchi |
| 2010/0008555 A1 | 1/2010 | Trumer et al. |
| 2010/0030061 A1 | 2/2010 | Canfield et al. |
| 2010/0039506 A1 | 2/2010 | Sarvestani et al. |
| 2010/0041949 A1 | 2/2010 | Tolkowsky |
| 2010/0054536 A1 | 3/2010 | Huang et al. |
| 2010/0080415 A1 | 4/2010 | Qureshi et al. |
| 2010/0113852 A1 | 5/2010 | Sydora |
| 2010/0121139 A1 | 5/2010 | OuYang et al. |
| 2010/0160733 A1 | 6/2010 | Gilboa |
| 2010/0161022 A1 | 6/2010 | Tolkowsky |
| 2010/0161129 A1 | 6/2010 | Costa et al. |
| 2010/0174178 A1 | 7/2010 | Edwards et al. |
| 2010/0225209 A1 | 9/2010 | Goldberg et al. |
| 2010/0240989 A1 | 9/2010 | Stoianovici et al. |
| 2010/0290530 A1 | 11/2010 | Huang et al. |
| 2010/0292565 A1 | 11/2010 | Meyer et al. |
| 2010/0298641 A1 | 11/2010 | Tanaka |
| 2010/0328455 A1 | 12/2010 | Nam et al. |
| 2011/0019878 A1 | 1/2011 | Soubelet et al. |
| 2011/0054303 A1 | 3/2011 | Barrick et al. |
| 2011/0092808 A1 | 4/2011 | Shachar et al. |
| 2011/0184238 A1 | 7/2011 | Higgins et al. |
| 2011/0234780 A1 | 9/2011 | Ito et al. |
| 2011/0238082 A1 | 9/2011 | Wenderow et al. |
| 2011/0245665 A1 | 10/2011 | Nentwick |
| 2011/0248987 A1 | 10/2011 | Mitchell |
| 2011/0249016 A1 | 10/2011 | Zhang et al. |
| 2011/0257480 A1 | 10/2011 | Takahashi et al. |
| 2011/0276179 A1 | 11/2011 | Banks et al. |
| 2011/0319910 A1 | 12/2011 | Roelle et al. |
| 2012/0046521 A1 | 2/2012 | Hunter et al. |
| 2012/0056986 A1 | 3/2012 | Popovic |
| 2012/0059248 A1 | 3/2012 | Holsing et al. |
| 2012/0062714 A1 | 3/2012 | Liu et al. |
| 2012/0065481 A1 | 3/2012 | Hunter et al. |
| 2012/0069167 A1 | 3/2012 | Liu et al. |
| 2012/0071782 A1 | 3/2012 | Patil et al. |
| 2012/0082351 A1 | 4/2012 | Higgins et al. |
| 2012/0120305 A1 | 5/2012 | Takahashi |
| 2012/0165656 A1 | 6/2012 | Montag et al. |
| 2012/0172712 A1 | 7/2012 | Bar-tal |
| 2012/0191079 A1 | 7/2012 | Moll et al. |
| 2012/0209069 A1 | 8/2012 | Popovic et al. |

(56) References Cited

U.S. PATENT DOCUMENTS

| | | |
|---|---|---|
| 2012/0215094 A1 | 8/2012 | Rahimian et al. |
| 2012/0219185 A1 | 8/2012 | Hu et al. |
| 2012/0289777 A1 | 11/2012 | Chopra et al. |
| 2012/0289783 A1 | 11/2012 | Duindam et al. |
| 2012/0302869 A1 | 11/2012 | Koyrakh et al. |
| 2013/0060146 A1 | 3/2013 | Yang et al. |
| 2013/0144116 A1 | 6/2013 | Cooper et al. |
| 2013/0204124 A1 | 8/2013 | Duindam et al. |
| 2013/0225942 A1 | 8/2013 | Holsing et al. |
| 2013/0243153 A1 | 9/2013 | Sra et al. |
| 2013/0246334 A1 | 9/2013 | Ahuja et al. |
| 2013/0259315 A1 | 10/2013 | Angot et al. |
| 2013/0303892 A1 | 11/2013 | Zhao et al. |
| 2013/0165945 A9 | 12/2013 | Roelle et al. |
| 2013/0345718 A1 | 12/2013 | Crawford et al. |
| 2014/0058406 A1 | 2/2014 | Tsekos |
| 2014/0107390 A1 | 4/2014 | Brown et al. |
| 2014/0114180 A1 | 4/2014 | Jain et al. |
| 2014/0142591 A1 | 5/2014 | Alvarez et al. |
| 2014/0148808 A1 | 5/2014 | Inkpen et al. |
| 2014/0180063 A1 | 6/2014 | Zhao et al. |
| 2014/0235943 A1 | 8/2014 | Paris et al. |
| 2014/0243849 A1 | 8/2014 | Saglam et al. |
| 2014/0257746 A1 | 9/2014 | Dunbar et al. |
| 2014/0264081 A1 | 9/2014 | Walker et al. |
| 2014/0275988 A1 | 9/2014 | Walker et al. |
| 2014/0276033 A1 | 9/2014 | Brannan et al. |
| 2014/0276937 A1 | 9/2014 | Wong et al. |
| 2014/0296655 A1 | 10/2014 | Akhbardeh et al. |
| 2014/0296657 A1 | 10/2014 | Izmirli et al. |
| 2014/0309527 A1 | 10/2014 | Namati et al. |
| 2014/0309649 A1 | 10/2014 | Alvarez et al. |
| 2014/0343416 A1 | 11/2014 | Panescu et al. |
| 2014/0350391 A1 | 11/2014 | Prisco et al. |
| 2014/0357953 A1 | 12/2014 | Roelle et al. |
| 2014/0357984 A1 | 12/2014 | Wallace et al. |
| 2014/0364739 A1 | 12/2014 | Liu et al. |
| 2014/0364870 A1 | 12/2014 | Alvarez et al. |
| 2014/0379000 A1 | 12/2014 | Romo et al. |
| 2015/0051482 A1 | 2/2015 | Liu et al. |
| 2015/0051592 A1 | 2/2015 | Kintz |
| 2015/0054929 A1 | 2/2015 | Ito et al. |
| 2015/0057498 A1 | 2/2015 | Akimoto et al. |
| 2015/0073266 A1 | 3/2015 | Brannan et al. |
| 2015/0101442 A1 | 4/2015 | Romo |
| 2015/0119638 A1 | 4/2015 | Yu et al. |
| 2015/0141808 A1 | 5/2015 | Elhawary et al. |
| 2015/0141858 A1 | 5/2015 | Razavi et al. |
| 2015/0142013 A1 | 5/2015 | Tanner et al. |
| 2015/0164594 A1 | 6/2015 | Romo et al. |
| 2015/0164596 A1 | 6/2015 | Romo et al. |
| 2015/0223725 A1 | 8/2015 | Engel et al. |
| 2015/0223897 A1 | 8/2015 | Kostrzewski et al. |
| 2015/0223902 A1 | 8/2015 | Walker et al. |
| 2015/0255782 A1 | 9/2015 | Kim et al. |
| 2015/0265087 A1 | 9/2015 | Messick, Jr. |
| 2015/0265368 A1 | 9/2015 | Chopra et al. |
| 2015/0275986 A1 | 10/2015 | Cooper |
| 2015/0287192 A1 | 10/2015 | Sasaki |
| 2015/0297133 A1 | 10/2015 | Jouanique-Dubuis et al. |
| 2015/0305650 A1 | 10/2015 | Hunter et al. |
| 2015/0313503 A1 | 11/2015 | Seibel et al. |
| 2015/0335480 A1 | 11/2015 | Alvarez et al. |
| 2016/0000302 A1 | 1/2016 | Brown et al. |
| 2016/0000414 A1 | 1/2016 | Brown et al. |
| 2016/0000520 A1 | 1/2016 | Lachmanovich et al. |
| 2016/0001038 A1 | 1/2016 | Romo et al. |
| 2016/0008033 A1 | 1/2016 | Hawkins et al. |
| 2016/0111192 A1 | 4/2016 | Suzara |
| 2016/0128992 A1 | 5/2016 | Hudson et al. |
| 2016/0183841 A1 | 6/2016 | Duindam et al. |
| 2016/0184032 A1 | 6/2016 | Romo et al. |
| 2016/0199134 A1 | 7/2016 | Brown et al. |
| 2016/0206389 A1 | 7/2016 | Miller et al. |
| 2016/0213432 A1 | 7/2016 | Flexman et al. |
| 2016/0228032 A1 | 8/2016 | Walker et al. |
| 2016/0270865 A1 | 9/2016 | Landey et al. |
| 2016/0287279 A1 | 10/2016 | Bovay et al. |
| 2016/0287346 A1 | 10/2016 | Hyodo et al. |
| 2016/0296294 A1 | 10/2016 | Moll et al. |
| 2016/0314710 A1 | 10/2016 | Jarc et al. |
| 2016/0331469 A1 | 11/2016 | Hall et al. |
| 2016/0349044 A1 | 12/2016 | Marell et al. |
| 2016/0360947 A1 | 12/2016 | Iida et al. |
| 2016/0372743 A1 | 12/2016 | Cho et al. |
| 2016/0374541 A1 | 12/2016 | Agrawal et al. |
| 2017/0007337 A1 | 1/2017 | Dan |
| 2017/0023423 A1 | 1/2017 | Jackson et al. |
| 2017/0055851 A1 | 3/2017 | Al-Ali et al. |
| 2017/0065364 A1 | 3/2017 | Schuh et al. |
| 2017/0065365 A1 | 3/2017 | Schuh |
| 2017/0079725 A1 | 3/2017 | Hoffman et al. |
| 2017/0079726 A1 | 3/2017 | Hoffman et al. |
| 2017/0084027 A1 | 3/2017 | Mintz et al. |
| 2017/0100199 A1 | 4/2017 | Yu et al. |
| 2017/0119411 A1 | 5/2017 | Shah |
| 2017/0119412 A1 | 5/2017 | Noonan et al. |
| 2017/0119413 A1 | 5/2017 | Romo |
| 2017/0119481 A1 | 5/2017 | Romo et al. |
| 2017/0165011 A1 | 6/2017 | Bovay et al. |
| 2017/0172673 A1 | 6/2017 | Yu et al. |
| 2017/0189118 A1 | 7/2017 | Chopra et al. |
| 2017/0202627 A1 | 7/2017 | Sramek et al. |
| 2017/0209073 A1 | 7/2017 | Sramek et al. |
| 2017/0215808 A1 | 8/2017 | Shimol et al. |
| 2017/0215969 A1 | 8/2017 | Zhai et al. |
| 2017/0238807 A9 | 8/2017 | Vertikov |
| 2017/0258366 A1 | 9/2017 | Tupin, Jr. et al. |
| 2017/0290631 A1 | 10/2017 | Lee et al. |
| 2017/0296032 A1 | 10/2017 | Li |
| 2017/0296202 A1 | 10/2017 | Brown |
| 2017/0303941 A1 | 10/2017 | Eisner |
| 2017/0325896 A1 | 11/2017 | Donhowe et al. |
| 2017/0333679 A1 | 11/2017 | Jiang |
| 2017/0340241 A1 | 11/2017 | Yamada |
| 2017/0340396 A1 | 11/2017 | Romo et al. |
| 2017/0348067 A1 | 12/2017 | Krimsky |
| 2017/0360418 A1 | 12/2017 | Wong et al. |
| 2017/0360508 A1 | 12/2017 | Germain et al. |
| 2017/0365055 A1 | 12/2017 | Mintz et al. |
| 2017/0367782 A1 | 12/2017 | Schuh et al. |
| 2018/0025666 A1 | 1/2018 | Ho et al. |
| 2018/0055576 A1 | 3/2018 | Koyrakh et al. |
| 2018/0055582 A1 | 3/2018 | Krimsky |
| 2018/0055583 A1 | 3/2018 | Schuh et al. |
| 2018/0098690 A1 | 4/2018 | Iwaki |
| 2018/0177383 A1 | 6/2018 | Noonan et al. |
| 2018/0177556 A1 | 6/2018 | Noonan |
| 2018/0214011 A1 | 8/2018 | Graetzel et al. |
| 2018/0217734 A1 | 8/2018 | Koenig et al. |
| 2018/0221038 A1 | 8/2018 | Noonan et al. |
| 2018/0221039 A1 | 8/2018 | Shah |
| 2018/0240237 A1 | 8/2018 | Donhowe et al. |
| 2018/0250083 A1 | 9/2018 | Schuh et al. |
| 2018/0271616 A1 | 9/2018 | Schuh et al. |
| 2018/0279852 A1 | 10/2018 | Rafii-Tari et al. |
| 2018/0280660 A1 | 10/2018 | Landey et al. |
| 2018/0286108 A1 | 10/2018 | Hirakawa |
| 2018/0289243 A1 | 10/2018 | Landey et al. |
| 2018/0289431 A1 | 10/2018 | Draper et al. |
| 2018/0308247 A1 | 10/2018 | Gupta |
| 2018/0325499 A1 | 11/2018 | Landey et al. |
| 2018/0333044 A1 | 11/2018 | Jenkins |
| 2018/0360435 A1 | 12/2018 | Romo |
| 2018/0368920 A1 | 12/2018 | Ummalaneni |
| 2019/0000559 A1 | 1/2019 | Berman et al. |
| 2019/0000560 A1 | 1/2019 | Berman et al. |
| 2019/0000566 A1 | 1/2019 | Graetzel et al. |
| 2019/0000568 A1 | 1/2019 | Connolly et al. |
| 2019/0000576 A1 | 1/2019 | Mintz et al. |
| 2019/0046814 A1 | 2/2019 | Senden et al. |
| 2019/0066314 A1 | 2/2019 | Abhari et al. |
| 2019/0083183 A1 | 3/2019 | Moll et al. |
| 2019/0086349 A1 | 3/2019 | Nelson et al. |

(56) References Cited

U.S. PATENT DOCUMENTS

| | | |
|---|---|---|
| 2019/0105776 A1 | 4/2019 | Ho et al. |
| 2019/0105785 A1 | 4/2019 | Meyer et al. |
| 2019/0107454 A1 | 4/2019 | Lin et al. |
| 2019/0110839 A1 | 4/2019 | Rafii-Tari et al. |
| 2019/0110843 A1 | 4/2019 | Ummalaneni |
| 2019/0117176 A1 | 4/2019 | Walker et al. |
| 2019/0117203 A1 | 4/2019 | Wong et al. |
| 2019/0125164 A1 | 5/2019 | Roelle et al. |
| 2019/0151148 A1 | 5/2019 | Alvarez et al. |
| 2019/0167366 A1 | 6/2019 | Ummalaneni et al. |
| 2019/0175009 A1 | 6/2019 | Mintz et al. |
| 2019/0175062 A1 | 6/2019 | Rafii-Tari et al. |
| 2019/0175287 A1 | 6/2019 | Hill et al. |
| 2019/0175799 A1 | 6/2019 | Hsu et al. |
| 2019/0183585 A1 | 6/2019 | Rafii-Tari et al. |
| 2019/0183587 A1 | 6/2019 | Rafii-Tari et al. |
| 2019/0216548 A1 | 7/2019 | Ummalaneni |
| 2019/0216550 A1 | 7/2019 | Eyre et al. |
| 2019/0216576 A1 | 7/2019 | Eyre et al. |
| 2019/0223974 A1 | 7/2019 | Romo et al. |
| 2019/0228525 A1 | 7/2019 | Mintz et al. |
| 2019/0228528 A1 | 7/2019 | Mintz et al. |
| 2019/0246882 A1 | 8/2019 | Graetzel et al. |
| 2019/0262086 A1 | 8/2019 | Connolly et al. |
| 2019/0269468 A1 | 9/2019 | Hsu et al. |
| 2019/0274764 A1 | 9/2019 | Romo |
| 2019/0287673 A1 | 9/2019 | Michihata et al. |
| 2019/0290109 A1 | 9/2019 | Agrawal et al. |
| 2019/0298160 A1 | 10/2019 | Ummalaneni et al. |
| 2019/0298460 A1 | 10/2019 | Al-Jadda et al. |
| 2019/0298465 A1 | 10/2019 | Chin et al. |
| 2019/0328213 A1 | 10/2019 | Landey et al. |
| 2019/0336238 A1 | 11/2019 | Yu et al. |
| 2019/0365201 A1 | 12/2019 | Noonan et al. |
| 2019/0365209 A1 | 12/2019 | Ye et al. |
| 2019/0365479 A1 | 12/2019 | Rafii-Tari |
| 2019/0365486 A1 | 12/2019 | Srinivasan et al. |
| 2019/0374297 A1 | 12/2019 | Wallace et al. |
| 2019/0375383 A1 | 12/2019 | Auer |
| 2019/0380787 A1 | 12/2019 | Ye et al. |
| 2019/0380797 A1 | 12/2019 | Yu et al. |
| 2020/0000530 A1 | 1/2020 | DeFonzo et al. |
| 2020/0000533 A1 | 1/2020 | Schuh et al. |
| 2020/0022767 A1 | 1/2020 | Hill et al. |
| 2020/0038123 A1 | 2/2020 | Graetzel et al. |
| 2020/0039086 A1 | 2/2020 | Meyer et al. |
| 2020/0046434 A1 | 2/2020 | Graetzel et al. |
| 2020/0054405 A1 | 2/2020 | Schuh et al. |
| 2020/0054408 A1 | 2/2020 | Schuh et al. |
| 2020/0055084 A1 | 2/2020 | Tian et al. |
| 2020/0060516 A1 | 2/2020 | Baez, Jr. |
| 2020/0078103 A1 | 3/2020 | Duindam et al. |
| 2020/0085516 A1 | 3/2020 | DeFonzo et al. |
| 2020/0093549 A1 | 3/2020 | Chin et al. |
| 2020/0093554 A1 | 3/2020 | Schuh et al. |
| 2020/0100845 A1 | 4/2020 | Julian |
| 2020/0100853 A1 | 4/2020 | Ho et al. |
| 2020/0100855 A1 | 4/2020 | Leparmentier et al. |
| 2020/0101264 A1 | 4/2020 | Jiang |
| 2020/0107894 A1 | 4/2020 | Wallace et al. |
| 2020/0121502 A1 | 4/2020 | Kintz |
| 2020/0146769 A1 | 5/2020 | Eyre et al. |
| 2020/0155084 A1 | 5/2020 | Walker et al. |
| 2020/0170630 A1 | 6/2020 | Wong et al. |
| 2020/0170720 A1 | 6/2020 | Ummalaneni |
| 2020/0171660 A1 | 6/2020 | Ho et al. |
| 2020/0188043 A1 | 6/2020 | Yu et al. |
| 2020/0197112 A1 | 6/2020 | Chin et al. |
| 2020/0206472 A1 | 7/2020 | Ma et al. |
| 2020/0217733 A1 | 7/2020 | Lin et al. |
| 2020/0222134 A1 | 7/2020 | Schuh et al. |
| 2020/0237458 A1 | 7/2020 | DeFonzo et al. |
| 2020/0261172 A1 | 8/2020 | Romo et al. |
| 2020/0268459 A1 | 8/2020 | Noonan |
| 2020/0268460 A1 | 8/2020 | Tse et al. |
| 2020/0281787 A1 | 9/2020 | Ruiz |
| 2020/0297437 A1 | 9/2020 | Schuh et al. |
| 2020/0297444 A1 | 9/2020 | Camarillo et al. |
| 2020/0305983 A1 | 10/2020 | Yampolsky et al. |
| 2020/0305989 A1 | 10/2020 | Schuh et al. |
| 2020/0305992 A1 | 10/2020 | Schuh et al. |
| 2020/0315717 A1 | 10/2020 | Bovay et al. |
| 2020/0315723 A1 | 10/2020 | Hassan et al. |
| 2020/0323596 A1 | 10/2020 | Moll et al. |
| 2020/0330167 A1 | 10/2020 | Romo et al. |
| 2020/0345216 A1 | 11/2020 | Jenkins |
| 2020/0352420 A1 | 11/2020 | Graetzel et al. |
| 2020/0360183 A1 | 11/2020 | Alvarez et al. |
| 2020/0367726 A1 | 11/2020 | Landey et al. |
| 2020/0367981 A1 | 11/2020 | Ho et al. |
| 2020/0375678 A1 | 12/2020 | Wallace et al. |

FOREIGN PATENT DOCUMENTS

| | | |
|---|---|---|
| CN | 102316817 A | 1/2012 |
| CN | 102458295 A | 5/2012 |
| CN | 102946801 A | 2/2013 |
| CN | 102973317 A | 3/2013 |
| CN | 103705307 A | 4/2014 |
| CN | 103735313 A | 4/2014 |
| CN | 103813748 A | 5/2014 |
| CN | 104758066 A | 7/2015 |
| CN | 105511881 A | 4/2016 |
| CN | 105559850 A | 5/2016 |
| CN | 105559886 A | 5/2016 |
| CN | 106455908 A | 2/2017 |
| CN | 106821498 A | 6/2017 |
| CN | 107427327 A | 12/2017 |
| CN | 108024699 A | 5/2018 |
| CN | 104931059 B | 9/2018 |
| EP | 3025630 A1 | 6/2016 |
| EP | 3600031 A1 | 2/2020 |
| JP | 2001000448 A | 1/2001 |
| JP | 2016529062 A | 9/2016 |
| KR | 1020140009359 A | 1/2014 |
| RU | 2569699 C2 | 11/2015 |
| WO | 2005078128 A1 | 8/2005 |
| WO | 2006051523 A2 | 5/2006 |
| WO | 2009097461 A1 | 8/2009 |
| WO | 2010065267 A1 | 6/2010 |
| WO | 2015089013 A1 | 6/2015 |
| WO | 2016054256 A1 | 4/2016 |
| WO | 2016077419 A1 | 5/2016 |
| WO | 2017030915 A1 | 2/2017 |
| WO | 2017036774 A1 | 3/2017 |
| WO | 2017048194 A1 | 3/2017 |
| WO | 2017049163 A1 | 3/2017 |
| WO | 2017066108 A1 | 4/2017 |
| WO | 2017821 A1 | 5/2017 |
| WO | 2017146890 A1 | 8/2017 |
| WO | 2017167754 A1 | 10/2017 |
| WO | 2018183727 A1 | 10/2018 |

OTHER PUBLICATIONS

Office action for U.S. Appl. No. 15/939,678, dated Jun. 3, 2019, 14 pages.
Office action for U.S. Appl. No. 15/939,678, dated Oct. 11, 2018, 14 pages.
Office action for U.S. Appl. No. 16/425,069, dated Jan. 7, 2020, 32 pages.
Office action for U.S. Appl. No. 16/425,069, dated Jul. 28, 2020, 24 pages.
Office Action for KR Appl. No. 1020187028219, dated Sep. 19, 2022, 2 pages.
Oh et al., dated May 2005, p. 5-75, Novel robotic catheter remote control system: safety and accuracy in delivering RF Lesions in all 4 cardiac chambers, Heart Rhythm, 2(5):S277-S278.
Point Cloud, Sep. 10, 2010, Wikipedia, 2 pp.
Preliminary Rejection for Appl. No. 1020207037356, dated Oct. 22, 2022, 3 pages.

(56) References Cited

OTHER PUBLICATIONS

Racadio et al., Dec. 2007, Live 3D guidance in the interventionail radiology suite, AJR, 189:W357-W364, 8 pages.
Reddy et al., May 2005, p. 1-53. Porcine pulmonary vein ablation using a novel robotic catheter control system and real-time integration of CT imaging with electroanatomical mapping, Hearth Rhythm, 2(5):S121, 1 page.
Ren et al., 2011, Multisensor data fusion in an integrated tracking system for endoscopic surgery, IEEE Transactions on Information Technology in Biomedicine, 16(1):106-111.
Sato et al., 2016, Techniques of stapler-based navigational thoracoscopic segmentectomy using virtual assisted lung mapping (VAL-MAP), Journal of Thoracic Disease, 8(Suppl 9):S716.
Shen et al., 2015, Robust camera localisation with depth reconstruction for bronchoscopic navigation. International Journal of Computer Assisted Radiology and Surgery, 10(6):801-813, 13 pages.
Shi et al., Sep. 14-18, 2014, Simultaneous catheter and environment modeling for trans-catheter aortic valve implantation, IEEE/RSJ International Conference on Intelligent Robots and Systems, pp. 2024-2202.
Slepian, dated 2010, Robotic Catheter Intervention: the Hansen Medical Sensei Robot Catheter System, PowerPoint presentation, 28 pages.
Solheim et ai., May 14, 2009, Navigated resection of giant intracranial meningiomas based on intraoperative 30 ultrasound, Acta Neurochir, 151:1143-1151.
Solomon et al., Dec. 2000, Three-dimensional CT Guided Bronchoscopy With a Real-Time Electromagnetic Position Sensor A Comparison of Two Image Registration Methods, Chest, 118(6):1783-1787.
Song et al., 2012, Autonomous and stable tracking of endoscope instrument tools with monocular camera, Advanced Intelligent Mechatronics (AIM), 2012 IEEE-ASME International Conference on.IEEE, 6 pages.
Vemuri et al., Dec. 2015, Inter-operative biopsy site relocations in endoluminal surgery, IEEE Transactions on Biomedical Engineering, Institute of Electrical and Electronics Engineers, < 10 .1109/ T8ME 2015.2503981 >, 13 pages.
Verdaasdonk et al., Jan. 23, 2012, Effect of Microsecond Pulse Length and Tip Shape on Explosive Bubble Formation of 2.78 μm Er,Cr;YSGG and 2.94 μm Er:YAG laser, Proceedings of SPIE, vol. 8221, 12, 1 pages.
Wilson et al., 2008, A Buyer's Guide to Electromagnetic Tracking Systems for Clinical Applications, Proc. of SPCI, 6918:691828-1, 12 pages.
Yip et al., 2012, Tissue tracking and registration for image-guided surgery, IEEE transactions on medical imaging 31(11 ):2169-2182, 14 pages.
Zhou et al., 2010, Synthesis of stereoscopic views from monocular endoscopic videos, Compute Vision and Pattern Recognition Workshops (CVPRVV), 2010 IEEE Computer Society Conference on IEE, 8 pages.
AU Examination Report for Appl. No. 2018243364, dated Apr. 21, 2023, 5 pages.
KR Preliminary Rejection for Appl. No. 10-2020-7037356, dated Mar. 10, 2023, 3 pages.
MX Office Action for Appl. No. MX/x/2020/012897, dated Nov. 24, 2023, 5 pages.
Notice of Preliminary Rejection for Appl. No. 1020217006777, dated Dec. 21, 2022, 8 pages.
Preliminary Rejection for KR Appl. No. 1020207037356, dated Oct. 26, 2022, 3 pages.
1 Decision of Patent Grant for Appl. No. 10-2020-7037356 dated May 16, 2023, 1 pages.
Examination Report for Appl. No. 18788077.0, dated Oct. 31, 2023, 4 pages.
CN Office Action for Appl. No. 201980036510.5, dated Aug. 24, 2023, 15 pages.
Notice of Acceptance for Appl. No. 2018243364, dated Sep. 25, 2023, 3 pages.
Advisory action for U.S. Appl. No. 15/939,678, dated Aug. 9, 2019, 3 pages.
Advisory action for U.S. Appl. No. 15/939,678, dated Sep. 8, 2020, 3 pages.
Advisory action for U.S. Appl. No. 16/425,069, dated Oct. 30, 2020, 3 pages.
Al-Ahmad et al., dated 2005, Early experience with a computerized robotically controlled catheter system, Journal of Interventional Cardiac Electrophysiology, 12:199-202, 4 pages.
Anant Vemuri et al., Inter-operative biopsy site relocations in endoluminal surgery, IEEE Transactions on Biomedical Engineering, Institute of Electrical and Electronics Engineers, Dec. 2015, 13 pages.
Bell et al., 2014, Six DOF Motion Estimation for Teleoperated Flexible Endoscopes Using Optical Flow: A Comparative Study, IEEE International Conference on Robotis and Automation, 8 pages.
Ciuti et al, 2012, Intra-Operative Monocular 3D Reconstruction for Image-Guided Navigation in Active Locomotion Capsule Endoscopy. Biomedical Robotics And Biomechatronics (Biorob), 4th IEEE Ras & Embs International Conference On IEEE, 7 pages.
CN office action for appl No. 201880001545, dated Jul. 20, 2021, 8 pages.
CN Office action for appl No. 201880001545, dated Oct. 20, 2020, 30 pages.
EP Search report for 18778077, dated Jan. 20, 2021,3 page.
EP Search Report for appl No. 19810872.2, dated Feb. 4, 2022, 12 pages.
EP written opinion for 18778077, dated Jan. 20, 2021, 4 page.
Fallavoliita et al., 2010, Acquiring Multiview C-Arm Images to Assist Cardiac Ablation Procedures, EURASIP Journal on Image and Video Processing, vol. 2010, Article ID 871408, pp. 1-10.
Gutierrez et al., Mar. 2008, A Practical Global Distortion Correction Method for an Image Intensifier Based X-Ray Fluoroscopy System, Med. Phys, 35(3):997-1007, 11 pages.
Haigron et al., 2004, Depth-map-based scene analysis for active navigation in virtual angioscopy, IEEE Transactions on Medical Imaging, 23( 11 ): 1380-1390, 11 pages.
Hansen Medical, Inc. 2005, System Overview, product brochure, 2 pp., dated as available at http://hansenmedical.com/system.aspx on Jul. 14, 2006 (accessed Jun. 25, 2019 using the internet archive way back machine).
Hansen Medical, Inc. Bibliography, product brochure, 1 p., dated as available athttp://hansenmedical.com/bibliography.aspx on Jul. 14, 2006 (accessed Jun. 25, 2019 using the internet archive way back machine).
Hansen Medical, Inc. dated 2007, Introducing the Sensei Robotic Catheter System, product brochure, 10 pages.
Hansen Medical, Inc. dated 2009, Sensei X Robotic Catheter System, product brochure, 3 pp.
Hansen Medical, Inc. Technology Advantages, product brochure, 1 p., dated as available at http://hansenmedical.com/advantages.aspx on Jul. 13, 2006 (accessed Jun. 25, 2019 using the internet archive way back machine).
International Search Report and Written Opinion dated Aug. 8, 2018 in application No. PCT/US18/25218, 15 pages.
International search report and written opinion dated Aug. 8, 2019 for PCT/US2019/034304, 14 pages.
JP Office Action for Appl. No. 2019553011, dated Mar. 15, 2022, 4 pages.
JP Office Action for Appl. No. 2019553011, dated Sep. 6, 2022, 2 pages.
JP Search Report for Appl. No. 2019553011, dated Jan. 13, 2022, 14 pages.
Kiraly et al, 2002, Three-dimensional Human Airway Segmentation Methods for Clinical Virtual Bronchoscopy, Acad Radio!, 9:1153-1168, 16 pages.
Kiraly et al., Sep. 2004, Three-dimensional path planning for virtual bronchoscopy, IEEE Transactions on Medical Imaging, 23(9):1365-1379, 15 pages.
Konen et al., 1998, The VN-project endoscopic image processing for neurosurgery, Computer Aided Surgery, 3:1-6 , 6 pages.

(56) References Cited

OTHER PUBLICATIONS

KR Office Action for appl. No. 1020187028219, dated Mar. 31, 2022, 1 page.
Kumar et al., 2014, Stereoscopic visualization of laparoscope image using depth information from 3D model, Computer methods and programs in biomedicine 113(3):862-868, 7 pages.
Livatino et al., 2015, Stereoscopic visualization and 3-D technologies in medical endoscopic teleoperation, IEEE, 11 pages.
Luo et al., 2010, Modified hybrid bronchoscope tracking based on sequential monte carlo sampler: Dynamic phantom validation, Asian Conference on Computer Vision. Springer, Berlin, Heidelberg, 13 pages.
Marrouche et al., dated May 6, 2005, AB32-1, Preliminary human experience using a novel robotic catheter remote control, Heart Rhythm, 2(5):S63, 1 page.
Mayo Clinic, Robotic Surgery, https://www.mayoclinic.org/tests-procedures/robotic-surgery/about/pac- 20394974?p=1, downloaded from the internet on Jul. 12, 2018, 2 pgs.
Mourgues et al., 2002, Flexible calibration of actuated stereoscopic endoscope for overlay in robot 672 assisted surgery, International Conference on Medical Image Computing and Computer-Assisted Intervention. SprinQer, Berlin, HeidelberQ, 10 pages.
Nadeem et al., 2016, Depth Reconstruction and Computer-Aided Polyp Detection in Optical Colonoscopy Video Frames, arXiv preprint arXiv:1609.01329, 12 pages.
Notice of allowance for U.S. Appl. No. 15/939,678, dated Aug. 30, 2021, 5 pages.
Notice of Allowance for U.S. Appl. No. 15/939,678, dated Dec. 17, 2021, 8 pages.
Notice of allowance for U.S. Appl. No. 15/939,678, dated Jun. 18, 2021, 8 pages.
Notice of allowance for U.S. Appl. No. 16/425,069, dated Apr. 14, 2021, 8 pages.
Notice of allowance for U.S. Appl. No. 16/425,069, dated Jul. 28, 2021, 8 pages.
Notice of Allowance for U.S. Appl. No. 16/425,069, dated Mar. 7, 2022, 5 pages.
Notice of Allowance for U.S. Appl. No. 16/425,069, dated Nov. 17, 2021, 5 pages.
Notice of Allowance for U.S. Appl. No. 15/939,678, dated Jun. 20, 2022, 8 pages.
Notice of Allowance for U.S. Appl. No. 15/939,678, dated Oct. 5, 2022, 5 pages.
Notice of Allowance for U.S. Appl. No. 16/425,069, dated Jul. 5, 2022, 5 pages.
Notice of Reasons for Refusal for JP Appl. No. 2019-553011, dated Aug. 29, 2022, 3 pages.
Office action for U.S. Appl. No. 15/939,678, dated Feb. 10, 2020, 15 pages.
Office action for U.S. Appl. No. 15/939,678, dated Feb. 11, 2019, 6 pages.
Office action for U.S. Appl. No. 15/939,678, dated Feb. 22, 2021, 14 pages.
CN 2nd Office Action and Search Report for Appl. No. 201980036510.5, dated Mar. 8, 2024, 14 pages.

ROBOTIC SYSTEMS FOR NAVIGATION OF LUMINAL NETWORKS THAT COMPENSATE FOR PHYSIOLOGICAL NOISE

CROSS-REFERENCE TO RELATED APPLICATION(S)

The present application is a continuation of U.S. patent application Ser. No. 15/939,678, filed on Mar. 29, 2018, entitled "ROBOTIC SYSTEMS FOR NAVIGATION OF LUMINAL NETWORKS THAT COMPENSATE FOR PHYSIOLOGICAL NOISE," which claims the benefit under 35 U.S.C. § 119(e) of U.S. Provisional Patent Application No. 62/480,257, filed on Mar. 31, 2017, entitled "ROBOTIC SYSTEMS FOR NAVIGATION OF LUMINAL NETWORKS THAT COMPENSATE FOR PHYSIOLOGICAL NOISE," the contents of each of which are hereby incorporated by reference herein in their entirety.

TECHNICAL FIELD

The systems and methods disclosed herein are directed to endoluminal procedures, and, more particularly, to endoluminal navigation.

BACKGROUND

Bronchoscopy is a medical procedure that allows a physician to examine the inside conditions of a patient's lung airways, such as bronchi and bronchioles. During the medical procedure, a thin, flexible tubular tool, known as a bronchoscope, may be inserted into the patient's mouth and passed down the patient's throat into his/her lung airways towards a tissue site identified for subsequent diagnosis and treatment. The bronchoscope can have an interior lumen (a "working channel") providing a pathway to the tissue site, and catheters and various medical tools can be inserted through the working channel to the tissue site.

SUMMARY

Pulmonologists can prevent intra-operative trauma by basing their decisions and actions on the respiratory cycle of the patient. One example of such an action is insertion of a biopsy tool to collect tissue samples, for example via bronchoscopy. At or near the periphery of the lung the airways may be narrow, and the circumference of the airways changes depending on the respiratory phase of the lung. The diameter of an airway expands as a patient inhales in the inspiration phase of the respiratory cycles and constricts as the patient exhales during the expiration phase of the cycle. During a procedure, a pulmonologist can observe the patient to determine whether they are in the inspiration phase or the expiration phase in order to decide whether a particular tool or endoscope of fixed diameter can enter the airway. An airway can close around a tool during expiration without causing trauma, however forcing a tool through a constricted airway during the expiration phase can cause critical trauma, for example by puncturing a blood vessel.

The aforementioned problems, among others, are addressed in some embodiment by the luminal network navigation systems and techniques described herein. Some embodiments of the disclosed luminal network navigation systems and techniques relate to incorporating respiratory frequency and/or magnitude into a navigation framework to implement patient safety measures (e.g., instrument control techniques, user interface alerts, notifications, and the like). As an example of an instrument control technique, a robotic system as described herein can automatically implement respiratory gating to prevent the user (a physician) from inadvertently causing trauma to patient airways. As used herein, "respiratory gating" can refer to the synchronization of an operation of an instrument in the airways of a patient with patient respiration. In some examples, this instrument control technique includes identifying regions ("caution zones") of patient airways in which instrument insertion during expiration is likely to cause trauma, for example smaller airways near the lung periphery where airway diameter during inhalation may approximate the instrument diameter. The robotic system can implement respiratory gating to control an instrument when the instrument is determined to be located within one of the identified regions. As an example of user interface alerts, the robotic system can present visual and/or auditory indicators of inspiration, expiration, and/or instrument positioning within an identified caution zone during a bronchoscopy procedure. A user can base instrument control on the user interface alerts, for example by manually performing respiratory gating or controlling the robotic system to perform respiratory gating.

Some embodiments of the disclosed bronchoscopy navigation systems and techniques relate to identifying, and compensating for, motion caused by patient respiration in order to provide a more accurate identification of the position of an instrument within patient airways. For example, an instrument positioned within patient airways can be provided with an electromagnetic (EM sensor). The navigation system can filter instrument position information from the EM sensor to remove signal noise due to cyclic motion of the respiratory passages caused by respiration. A frequency of the cyclic respiratory motion can be obtained from data from one or more additional sensors. In some implementations, inspiration and expiration cycles can be determined based on data from additional EM sensor(s), accelerometer(s), and/or acoustic respiratory sensor(s) placed on the body of the patient in one example. In some implementations, the frequency can be obtained from other types of sensors or systems, for example respiratory cycle information from a ventilator used to control patient breathing, or respiratory cycle information extracted from automated analysis of images received from an optical sensor positioned to observe the patient.

Accordingly, one aspect relates to a system configured to navigate a luminal network of a patient, the system comprising a field generator configured to generate an electromagnetic (EM) field; a set of one or more EM sensors at a distal end of a steerable instrument; a set of one or more respiration sensors; at least one computer-readable memory having stored thereon executable instructions; and one or more processors in communication with the at least one computer-readable memory and configured to execute the instructions to cause the system to at least access a preoperative model representative of the luminal network; access a mapping between a coordinate frame of the EM field and a coordinate frame of the preoperative model; calculate at least one position of the set of EM sensors within the EM field based on a data signal from the set of EM sensors; calculate a frequency of respiration of the patient based on a data signal from the set of respiration sensors; and determine a position of the distal end of the steerable instrument relative to the preoperative model based on the registration mapping, the frequency of the respiration, and the at least one position of the set of EM sensors within the EM field.

In some implementations, each EM sensor of the set of EM sensors is configured to produce a signal indicative of a distance and angle between the EM sensor and the field generator, the electrical signal usable to determine one or both of a position and orientation of the EM sensor within the EM field.

In some implementations, the one or more processors are configured to execute the instructions to cause the system to at least transform one or more data signals from the set of respiration sensors into a frequency domain representation of the one or more data signals; and identify the frequency of respiration from the frequency domain representation of the one or more data signals. In some implementations, the one or more processors are configured to execute the instructions to cause the system to at least apply a filter to one or more data signals from the set of EM sensors, the filter configured to attenuate a portion of the one or more data signals with the identified frequency; and determine the position of the distal end of the steerable instrument relative to the preoperative model based on the filtered one or more data signals from the set of EM sensors.

In some implementations, the one or more processors are configured to execute the instructions to cause the system to at least calculate at least one magnitude of displacement of the set of respiration sensors between inspiration and expiration phases of the respiration of the patient. In some implementations, the one or more processors are configured to execute the instructions to at least determine at least one position of the set of EM sensors relative to the set of respiration sensors; calculate at least one positional displacement of the set of EM sensors between the inspiration and the expiration phases based on (i) the determined at least one position of the set of EM sensors relative to the set of respiration sensors and (ii) the at least one magnitude of displacement of the set of respiration sensors between inspiration and expiration phases; and determine the position of the distal end of the steerable instrument relative to the preoperative model based on the calculated at least one positional displacement of the set of EM sensors between the inspiration and the expiration phases. In some implementations, the set of respiration sensors comprises a first additional EM sensor positioned, in use, at a first position on the body surface and a second additional EM sensor positioned, in use, at a second position of the body surface, wherein the second position is spaced apart from the first position such that a first magnitude of displacement of the first additional EM sensor is greater than a second magnitude of displacement of the second additional EM sensor between the inspiration and the expiration phases. In some implementations, the one or more processors are configured to execute the instructions to cause the system to at least determine a relative positioning of the set of EM sensors with respect to the first and second additional EM sensors; and interpolate between the first and second magnitudes of displacement based on the determined relative positioning of the set of EM sensors, wherein the calculation of the positional displacement of the set of EM sensors between the inspiration and the expiration phases is based on the interpolated magnitude. In some implementations, the one or more processors are configured to execute the instructions cause the system to at least estimate a movement vector for at least a portion of the preoperative model based on the calculated at least one magnitude of displacement; translate the preoperative model within the coordinate frame of the EM field based on the estimated movement vector; and determine the position of the distal end of the steerable instrument based on the translated preoperative model. In some implementations, to translate the preoperative model within the coordinate frame of the EM field, the one or more processors are configured to execute the instructions cause the system to at least move a first portion of the model to first new coordinates based on the first magnitude of displacement; and move a second portion of the model to second new coordinates based on the second magnitude of displacement.

Some implementations further comprise a robotic system having instrument drivers configured to effect movement of the steerable instrument. In some implementations, the one or more processors are configured to execute the instructions to cause the system to at least identify a next movement of the steerable instrument based on the position of the distal end of the steerable instrument relative to the preoperative model; and direct actuation of the instrument drivers to effect the next movement. Some implementations further comprise a display, wherein the one or more processors are configured to execute the instructions to cause the system to at least generate a graphical representation of the position of the distal end of the steerable instrument relative to the preoperative model; and render the generated graphical representation on the display. In some implementations, the robotic system comprises an input device configured to control movement of the steerable instrument based on user manipulation of the input device.

In some implementations, the preoperative model comprises a three-dimensional computed tomography model of the luminal network of the patient.

Another aspect relates to an apparatus configured to determine navigation of a luminal network of a patient, the apparatus comprising at least one computer-readable memory having stored thereon executable instructions; and one or more processors in communication with the at least one computer-readable memory and configured to execute the instructions to cause the apparatus to at least access a model representative of the luminal network; access a mapping between a coordinate frame of the model and a coordinate frame of an electromagnetic (EM) field generated around the luminal network; receive data from an EM sensor on a distal end of a steerable instrument inserted, in use, into the luminal network; calculate, based on data from the EM sensor, a position of the EM sensor within the EM field based on data from the EM sensor; receive data from at least one additional sensor configured to detect movement of the luminal network; calculate, based on data from the at least one additional sensor, a frequency of cyclic movement of the luminal network; and determine a position of the distal end of the steerable instrument relative to the model based on the mapping, the frequency, and the position of the EM sensor within the EM field.

In some implementations, the at least one additional sensor comprises one or more EM sensors.

In some implementations, the at least one additional sensor comprises an accelerometer.

In some implementations, the at least one additional sensor comprises an acoustic respiratory sensor, and the acoustic respiratory sensor detects the cyclic movement during patient respiration.

In some implementations, the luminal network comprises respiratory airways, wherein the one or more processors are configured to execute the instructions to cause the apparatus to guide the steerable instrument through the luminal network.

In some implementations, the one or more processors are configured to execute the instructions to cause the system to at least transform one or more data signals from the at least one additional sensor into a frequency domain representation of the one or more data signals; and identify the frequency of cyclic movement from the frequency domain representation of the one or more data signals. In some implementations, the one or more processors are configured to execute the instructions to cause the system to at least apply a filter to one or more data signals from the EM sensor, the filter configured to attenuate a portion of the one or more data signals with the identified frequency; and determine the position of the distal end of the steerable instrument relative to the model based on the filtered one or more data signals from the EM sensor.

In some implementations, the luminal network comprises respiratory airways, and the one or more processors are configured to execute the instructions to cause the system to at least calculate at least one magnitude of displacement of the at least one additional sensor between inspiration and expiration phases of the respiration of the patient. In some implementations, the one or more processors are configured to execute the instructions to at least determine a position of the EM sensor relative to the at least one additional sensor; calculate a positional displacement of the EM sensor between the inspiration and the expiration phases based on (i) the determined position of the EM sensor relative to the at least one additional sensor and (ii) the at least one magnitude of displacement of the at least one additional sensor between inspiration and expiration phases; and determine the position of the distal end of the steerable instrument relative to the preoperative model based on the calculated positional displacement of EM sensor between the inspiration and the expiration phases. In some implementations, the at least one additional sensor comprises a first additional EM sensor positioned, in use, at a first position on the body surface and a second additional EM sensor positioned, in use, at a second position of the body surface, wherein the second position is spaced apart from the first position such that a first magnitude of displacement of the first additional EM sensor is greater than a second magnitude of displacement of the second additional EM sensor between the inspiration and the expiration phases. In some implementations, the one or more processors are configured to execute the instructions to cause the system to at least determine a position of the EM sensor relative to the first and second additional EM sensors; and interpolate between the first and second magnitudes of displacement based on the determined position of the EM sensor relative to the first and second additional EM sensors, wherein the calculation of the positional displacement of the EM sensor between the inspiration and the expiration phases is based on the interpolated magnitude. In some implementations, the one or more processors are configured to execute the instructions cause the system to at least estimate a movement vector for at least a portion of the model based on the calculated at least one magnitude of displacement; translate the model within the coordinate frame of the EM field based on the estimated movement vector; and determine the position of the distal end of the steerable instrument based on the translated model. In some implementations, to translate the preoperative model within the coordinate frame of the EM field, the one or more processors are configured to execute the instructions cause the system to at least move a first portion of the model to first new coordinates based on the first magnitude of displacement; and move a second portion of the model to second new coordinates based on the second magnitude of displacement.

Another aspect relates to a non-transitory computer readable storage medium having stored thereon instructions that, when executed, cause at least one computing device to at least receive first data from an electromagnetic (EM) sensor on an instrument inserted, in use, in a tissue site of a patient and second data from at least one additional sensor configured to detect movement of the tissue site; calculate, based on the first data, a position of the EM sensor within an EM field disposed around the tissue site; calculate, based on second data, a frequency of cyclic movement of the tissue site; and determine a position of the instrument relative to the tissue site based on (i) the frequency of cyclic movement of the tissue site and (ii) the position of the EM sensor within the field.

In some implementations, the instructions, when executed, cause the at least one computing device to transform the second data into a frequency domain representation; and identify the frequency of the cyclic movement from the frequency domain representation. In some implementations, the instructions, when executed, cause the at least one computing device to apply a filter to the first data, the filter configured to attenuate a portion of the first data with the identified frequency; and determine the position of the instrument based on the filtered first data.

In some implementations, the tissue site comprises respiratory airways, and the instructions, when executed, cause the at least one computing device to calculate at least one magnitude of displacement of the at least one additional sensor between inspiration and expiration phases of the respiration of the patient. In some implementations, the instructions, when executed, cause the at least one computing device to determine a position of the EM sensor relative to the at least one additional sensor; calculate a positional displacement of the EM sensor between the inspiration and the expiration phases based on (i) the determined position of the EM sensor relative to the at least one additional sensor and (ii) the at least one magnitude of displacement of the at least one additional sensor between inspiration and expiration phases; and determine the position of the distal end of the steerable instrument relative to the preoperative model based on the calculated positional displacement of EM sensor between the inspiration and the expiration phases. In some implementations, the at least one additional sensor comprises a first additional EM sensor positioned, in use, at a first position on the patient and a second additional EM sensor positioned, in use, at a second position of the patient, wherein the second position is spaced apart from the first position such that a first magnitude of displacement of the first additional EM sensor is greater than a second magnitude of displacement of the second additional EM sensor between the inspiration and the expiration phases, and the instructions, when executed, cause the at least one computing device to determine a position of the EM sensor relative to the first and second additional EM sensors; and interpolate between the first and second magnitudes of displacement based on the determined position of the EM sensor relative to the first and second additional EM sensors, wherein the calculation of the positional displacement of the EM sensor between the inspiration and the expiration phases is based on the interpolated magnitude.

In some implementations, the instructions, when executed, cause the at least one computing device to access data representing a model representing a topography of the tissue site; and a mapping between coordinate frames of the field and the model, wherein determining the position of the instrument is based on the mapping, the frequency, and the position of the EM sensor within the field. In some implementations, the tissue site comprises respiratory airways, and the instructions, when executed, cause the at least one computing device to calculate at least one magnitude of displacement of the at least one additional sensor between inspiration and expiration phases of the respiration of the patient; estimate a movement vector for at least a portion of the model based on the calculated at least one magnitude of displacement; translate the model within a coordinate frame based on the estimated movement vector; and determine the position of the instrument based on the translated model. In some implementations, to translate the model within the coordinate frame, the instructions, when executed, cause the at least one computing device to move a first portion of the model to first new coordinates based on the first magnitude of displacement; and move a second portion of the model to second new coordinates based on the second magnitude of displacement.

Another aspect relates to a method, comprising receiving first data from a first sensor on an instrument inserted, in use, in a tissue site of a patient and second data from at least one additional sensor configured to detect movement of the tissue site; calculating, based on the first data, a position of the first sensor within a volume around the tissue site; calculating, based on second data, a frequency of cyclic movement of the tissue site; determining a position of the instrument relative to the tissue site based on the frequency and the position of the first sensor within the volume.

Some implementations can be performed by one or more hardware processors.

Some implementations further comprise transforming the second data into a frequency domain representation; and identifying the frequency of the cyclic movement from the frequency domain representation.

Some implementations further comprise applying a filter to the first data, the filter configured to attenuate a portion of the first data with the identified frequency; and determining the position of the instrument based on the filtered first data.

In some implementations, the tissue site comprises respiratory airways, and the method further comprises calculating at least one magnitude of displacement of the at least one additional sensor between inspiration and expiration phases of the respiration of the patient. Some implementations further comprise determining a position of the first sensor relative to the at least one additional sensor; calculating a positional displacement of the first sensor between the inspiration and the expiration phases based on (i) the determined position of the first sensor relative to the at least one additional sensor and (ii) the at least one magnitude of displacement of the at least one additional sensor between inspiration and expiration phases; and determining the position of the instrument relative based on the calculated positional displacement of first sensor between the inspiration and the expiration phases. In some implementations, the at least one additional sensor comprises a first additional sensor positioned, in use, at a first position on the patient and a second additional sensor positioned, in use, at a second position of the patient, wherein the second position is spaced apart from the first position such that a first magnitude of displacement of the first additional sensor is greater than a second magnitude of displacement of the second additional sensor between the inspiration and the expiration phases, and the method further comprises determining a position of the first sensor relative to the first and second additional sensors; and interpolating between the first and second magnitudes of displacement based on the determined position of the first sensor relative to the first and second additional sensors, wherein the calculation of the positional displacement of the first sensor between the inspiration and the expiration phases is based on the interpolated magnitude.

Some implementations further comprise accessing data representing a model representing a topography of the tissue site, and a mapping between coordinate frames of the field and the model; determining the position of the instrument is based on the mapping, the frequency, and the position of the EM sensor within the field. In some implementations, the tissue site comprises respiratory airways, and the method further comprises calculating at least one magnitude of displacement of the at least one additional sensor between inspiration and expiration phases of the respiration of the patient; estimating a movement vector for at least a portion of the model based on the calculated at least one magnitude of displacement; translating the model within a coordinate frame based on the estimated movement vector; and determining the position of the instrument based on the translated model. Some implementations further comprise translating the model within the coordinate frame based on moving a first portion of the model to first new coordinates based on the first magnitude of displacement; and moving a second portion of the model to second new coordinates based on the second magnitude of displacement.

Another aspect relates to a system configured to navigate a luminal network of a patient, the system comprising a field generator configured to generate an electromagnetic (EM) field; a set of one or more EM sensors including at a distal end of a steerable instrument; at least one respiration sensor; at least one computer-readable memory having stored thereon executable instructions; and one or more processors in communication with the at least one computer-readable memory and configured to execute the instructions to cause the system to at least access a preoperative model representative of the luminal network; access a mapping between a coordinate frame of the EM field and a coordinate frame of the preoperative model; calculate a position of the set of EM sensors within the EM field based on a data signal from the set of EM sensors; determine a position of the distal end of the steerable instrument relative to the preoperative model based on the mapping and the position of the set of EM sensors within the EM field; determine, based on data from the at least one respiration sensor, whether a respiration phase of the patient during acquisition of the data signal from the set of EM sensors corresponds to an inspiration phase or an expiration phase; and determine whether to activate a safety mode for a next movement of the steerable instrument based on the position of the distal end of the steerable instrument relative to the model and the respiration phase.

In some implementations, the one or more processors are configured to execute the instructions to cause the system to activate the safety mode and, in the safety mode, implement one or more safety features to guide synchronization of the next movement with the respiration phase.

In some implementations, the one or more processors are configured to execute the instructions to cause the system to access information regarding a navigation path through the luminal network to a target tissue site; identify, based on the navigation path and the position of the distal end of the steerable instrument relative to the preoperative model, that the distal end of the steerable instrument is positioned, in use, within a predefined safety zone of the luminal network; and activate the safety mode based on determining that the distal end of the steerable instrument is positioned within the predefined safety zone. In some implementations, the navigation path includes a plurality of zones, and the safety zone is located in a portion of the luminal network where a difference between a respiratory passage diameter and a diameter of the distal end of the steerable instrument falls below a predetermined value.

In some implementations, in the safety mode, the one or more processors are configured to execute the instructions to cause the system to output information representative of the respiration phase to a user.

Some implementations further comprise a robotic system comprising a display; an input device configured to generate signals to control movement of the steerable instrument responsive to user manipulation of the input device; and instrument drivers configured to effect movement of the steerable instrument based on the signals from the input device. In some implementations, the one or more processors are configured to execute the instructions to cause the system to, in response to activating the safety mode, prevent actuation of the instrument drivers during expiration phases of the respiration of the patient. In some implementations, the one or more processors are configured to execute the instructions to cause the system to prevent the actuation of the instrument drivers by overriding attempted actuation of the instrument drivers based on user manipulation of the input device. In some implementations, the one or more processors are configured to execute the instructions to cause the system to output a graphical representation of inspiration and expiration phases of the respiration, the graphical representation displayable on the display.

In some implementations, the preoperative model comprises a three-dimensional computed tomography model of the luminal network of the patient.

Another aspect relates to an apparatus configured to guide navigation of a luminal network of a patient, the apparatus comprising at least one computer-readable memory having stored thereon executable instructions; and one or more processors in communication with the at least one computer-readable memory and configured to execute the instructions to cause the apparatus to at least access data corresponding to a model representative of the luminal network, a mapping between a coordinate frame of the model and a coordinate frame of an electromagnetic (EM) field generated around the luminal network, a signal from an EM sensor on a distal end of a steerable instrument inserted, in use, into the luminal network, and a signal from at least one additional sensor configured to detect movement of the luminal network; calculate a position of the EM sensor within the EM field based on the data corresponding to the signal from the EM sensor; calculate a next movement of the steerable instrument based on the position of the distal end of the steerable instrument relative to the model; determine, based on the data corresponding to the signal from the at least one additional sensor, whether a respiration phase of the patient during acquisition of the signal from the first sensor corresponds to an inspiration phase or an expiration phase; and determine whether to activate a safety mode for the next movement of the steerable instrument based on the respiration phase.

In some implementations, the at least one additional sensor comprises one or more EM sensors.

In some implementations, the at least one additional sensor comprises an accelerometer.

In some implementations, the at least one additional sensor comprises an acoustic respiratory sensor configured to detect the cyclic movement during patient respiration.

In some implementations, the one or more processors are configured to execute the instructions to cause the system to activate the safety mode and, in the safety mode, implement one or more safety features to guide synchronization of the next movement with the respiration phase.

In some implementations, the one or more processors are configured to execute the instructions to cause the system to access information regarding a navigation path through the luminal network to a target tissue site; identify, based on the navigation path and the position of the distal end of the steerable instrument relative to the preoperative model, that the distal end of the steerable instrument is positioned, in use, within a predefined safety zone of the luminal network; and activate the safety mode based on determining that the distal end of the steerable instrument is positioned within the predefined safety zone. In some implementations, the navigation path includes a plurality of zones, and the safety zone is located in a portion of the luminal network where a difference between a respiratory passage diameter and a diameter of the distal end of the steerable instrument falls below a predetermined value. In some implementations, in the safety mode, the one or more processors are configured to execute the instructions to cause the system to output information representative of the respiration phase to a user.

Some implementations further comprise a robotic system comprising a display; an input device configured to generate signals to control movement of the steerable instrument responsive to user manipulation of the input device; and instrument drivers configured to effect movement of the steerable instrument based on the signals from the input device. In some implementations, the one or more processors are configured to execute the instructions to cause the system to, in response to activating the safety mode, prevent actuation of the instrument drivers during one or more expiration phases of the respiration of the patient In some implementations, the one or more processors are configured to execute the instructions to cause the system to prevent the actuation of the instrument drivers by overriding attempted actuation of the instrument drivers based on user manipulation of the input device. In some implementations, the one or more processors are configured to execute the instructions to cause the system to output a graphical representation of inspiration and expiration phases of the respiration, the graphical representation displayable on the display.

Another aspect relates to a non-transitory computer readable storage medium having stored thereon instructions that, when executed, cause a processor of a device to at least receive first data from a first sensor on an instrument inserted, in use, in a luminal network of a patient and second data from at least one additional sensor configured to detect movement of the luminal network; calculate a position of the first sensor within a field disposed around the tissue site based on the first data; determine, based on the second data, whether a respiration phase of the patient during acquisition of the first data from the first sensor corresponds to an inspiration phase or an expiration phase; determine a position of the instrument based on the mapping and the position of the first sensor within the field; and determine whether to activate a safety mode based on the position of the instrument and the respiration phase.

In some implementations, the instructions, when executed, cause the processor to at least receive image data from the at least one additional sensor and, based on the image data, determine whether the respiration phase corresponds to the inspiration phase or the expiration phase.

In some implementations, the instructions, when executed, cause the processor to at least receive accelerometer data from the at least one additional sensor and, based a direction of movement indicated by the accelerometer data, determine whether the respiration phase corresponds to the inspiration phase or the expiration phase.

In some implementations, the instructions, when executed, cause the processor to at least access data corresponding to (i) a model representing topography of the luminal network, and (ii) a mapping between coordinate frames of the field and the model; wherein determining the position of the instrument comprises determining a position of the instrument relative to the model based on the mapping and the position of the first sensor within the field.

In some implementations, the instructions, when executed, cause the processor to at least activate the safety mode and, in the safety mode, implement one or more safety features to guide synchronization of a next movement with the respiration phase.

In some implementations, the instructions, when executed, cause the processor to at least access information regarding a navigation path through the luminal network to a target tissue site; identify, based on the navigation path and the position of the instrument, that the instrument is positioned, in use, within a predefined safety zone of the luminal network; and activate the safety mode based on determining that the instrument is positioned within the predefined safety zone. In some implementations, the navigation path includes a plurality of zones, and the safety zone is located in a portion of the luminal network where a difference between a respiratory passage diameter and a diameter of the distal end of the steerable instrument falls below a predetermined value.

In some implementations, the instructions, when executed, cause the processor to at least, in response to determining to activate the safety mode, output information representative of the respiration phase to a user.

In some implementations, the instructions, when executed, cause the processor to at least, in response to determining to activate the safety mode, prevent actuation of robotic instrument drivers during expiration phases of the respiration of the patient, the robotic instrument drivers configured to effect movement of the instrument through the luminal network.

Another aspect relates to a method comprising receiving first data from a first sensor on an instrument inserted, in use, in a luminal network of a patient and second data from at least one additional sensor configured to detect movement of the luminal network; calculating a position of the first sensor within a field disposed around the tissue site based on the first data; determining, based on the second data, whether a respiration phase of the patient during acquisition of the first data from the first sensor corresponds to an inspiration phase or an expiration phase; determining a position of the instrument based on the position of the first sensor within the field; determining a next movement of the instrument based on the position; and determining whether to activate a safety mode for the next movement based on the respiration phase.

Some implementations can be performed by one or more hardware processors.

Some implementations further comprise activating the safety mode; and in the safety mode, implementing one or more safety features to guide synchronization of the next movement with the respiration phase.

Some implementations further comprise accessing data corresponding to (i) a model representing topography of the luminal network, and (ii) a mapping between coordinate frames of the field and the model; wherein determining the position of the instrument comprises determining a position of the instrument relative to the model based on the mapping and the position of the first sensor within the field.

Some implementations further comprise accessing information regarding a navigation path through the luminal network to a target tissue site; identifying, based on the navigation path and the position of the instrument, that the instrument is positioned, in use, within a predefined safety zone of the luminal network; and activating the safety mode based on determining that the instrument is positioned within the predefined safety zone.

Some implementations further comprise, in response to determining to activate the safety mode, outputting information representative of the respiration phase to a user.

Some implementations further comprise, in response to determining to activate the safety mode, preventing actuation of robotic instrument drivers during expiration phases of the respiration of the patient, the robotic instrument drivers configured to effect movement of the instrument through the luminal network. In some implementations, preventing the actuation of the robotic instrument drivers comprises overriding a user input to perform the next movement during the expiration phase or a subsequent expiration phase.

BRIEF DESCRIPTION OF THE DRAWINGS

The disclosed aspects will hereinafter be described in conjunction with the appended drawings and appendices, provided to illustrate and not to limit the disclosed aspects, wherein like designations denote like elements.

DETAILED DESCRIPTION

Introduction

Figure 1A:
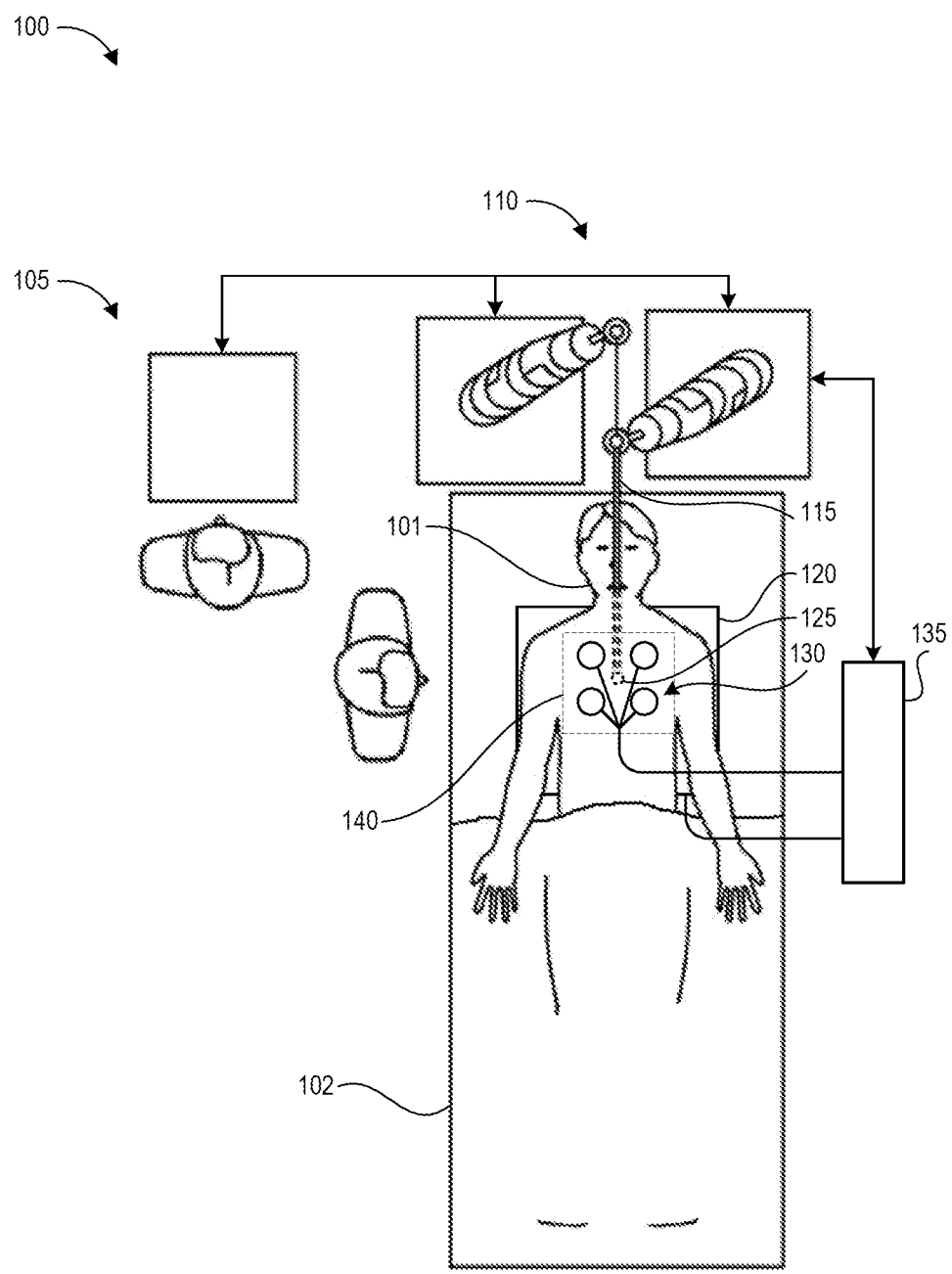
FIG. 1A illustrates an example operating environment implementing the disclosed navigation systems and techniques.

Embodiments of the disclosure relate to systems and techniques that facilitate navigation through luminal networks, for example lung airways, by analyzing multiple navigation-related data sources to increase accuracy in estimation of location and orientation of a medical instrument within the luminal network, by filtering instrument position data to remove noise from cyclic movement of the luminal network, and/or by activating respiratory gating and other types of safety features that modify navigation control based on the cyclic movement.

A bronchoscope can include a light source and a small camera that allows a physician to inspect a patient's windpipe and airways. Patient trauma can occur if the precise location of the bronchoscope within the patient airways is not known. To ascertain the location of the bronchoscope, image-based bronchoscopy guidance systems can use data from the bronchoscope camera to perform local registrations (e.g., registrations at a particular location within a luminal network) at bifurcations of patient airways and so beneficially can be less susceptible to position errors due to patient breathing motion. However, as image-based guidance methods rely on the bronchoscope video, they can be affected by artifacts in bronchoscope video caused by patient coughing or mucous obstruction, etc.

Electromagnetic navigation-guided bronchoscopy (EMN bronchoscopy) is a type of bronchosopic procedure that implements electromagnetic (EM) technology to localize and guide endoscopic tools or catheters through the bronchial pathways of the lung. EMN bronchoscopy systems can use an EM field generator that emits a low-intensity, varying EM field and establishes the position of the tracking volume around the luminal network of the patient. The EM field is a physical field produced by electrically charged objects that affects the behavior of charged objects in the vicinity of the field. EM sensors attached to objects positioned within the generated field can be used to track locations and orientations of these objects within the EM field. Small currents are induced in the EM sensors by the varying electromagnetic field. The characteristics of these electrical signals are dependent on the distance and angle between a sensor and the EM field generator. Accordingly, an EMN bronchoscopy system can include an EM field generator, a steerable channel having an EM sensor at or near its distal tip, and a guidance computing system. The EM field generator generates an EM field around the luminal network of the patient to be navigated, for example airways, gastrointestinal tract, or a circulatory pathway. The steerable channel is inserted through the working channel of the bronchoscope and tracked in the EM field via the EM sensor.

Prior to the start of an EMN bronchoscopy procedure, a virtual, three-dimensional (3D) bronchial map can be obtained for the patient's specific airway structure, for example from a preoperative computed tomography (CT) chest scan. Using the map and an EMN bronchoscopy system, physicians can navigate to a desired location within the lung to biopsy lesions, stage lymph nodes, insert markers to guide radiotherapy or guide brachytherapy catheters. For example, a registration can be performed at the beginning of a procedure to generate a mapping between the coordinate system of the EM field and the model coordinate system. Thus, as the steerable channel is tracked during bronchoscopy, the steerable channel's position in the model coordinate system becomes nominally known based on position data from the EM sensor. However, the patient's breathing causes chest movement that can lead to errors in correlating the position of the steerable instrument and/or model with the coordinate frame of the EM field. These errors can be magnified in the peripheral airways, as the airway branches become smaller and experience greater movement due to patient respiration.

As used herein, a coordinate frame is the frame of reference of a particular sensing modality. For example, for EM data the EM coordinate frame is the frame of reference defined by the source of the EM field (e.g., the field generator). For CT images and for a segmented 3D model, this frame of reference is based on the frame defined by the scanner. The present navigation systems address the problem of navigation of representing (register) these different sources of data (which are in their own frames of reference) to the 3D model (i.e. the CT frame), for example in order to display the location of the instrument inside the model.

Accordingly, as described in more detail below, the disclosed luminal network navigation systems and techniques can combine input from both image-based navigation systems, robotic systems, and EM navigation systems, as well as input from other patient sensors, in order to mitigate navigational problems and enable more effective endoscopy procedures. For example, a navigation fusion framework can analyze image information received from an instrument camera, position information from an EM sensor on the instrument tip, and robotic position information from a robotic system guiding movement of the instrument. Based on the analysis, the navigation fusion framework can base instrument position estimates and/or navigation decisions on one or more of these types of navigation data. Some implementations of the navigation fusion framework can further determine instrument position relative to a 3D model of the luminal network. In some embodiments, the instrument position information from the EM sensor can be filtered to remove signal noise due to cyclic motion of the luminal network, for example due to respiration in airway navigation or due to pulsatile blood flow in circulatory system navigation. A frequency of the cyclic motion can be obtained from data from one or more additional sensors. For example, inspiration and expiration cycles can be determined based on data from additional EM sensor(s), accelerometer(s), and/or acoustic respiratory sensor(s) placed on the body of the patient and/or optical sensors positioned with a field of view to observe the movement of the patient. Some embodiments can implement navigation safety features based on one or both of instrument position and cyclic motion of the luminal network. For example, in a bronchoscopy implementation, the safety features can include display of respiration cycle information and/or limitations imposed on instrument insertion during expiration.

The disclosed systems and techniques can provide advantages for bronchoscopy guidance systems and other applications, including other types of endoscopic procedures for navigation of luminal networks. In anatomy, a "lumen" may refer to the inner open space or cavity of a tubular organ, as of an airway, a blood vessel, or an intestine. As used herein, a "luminal network" refers to an anatomical structure having at least one lumen leading towards a target tissue site, for example the airways of the lungs, the circulatory system, and the gastrointestinal system. Thus, although the present disclosure provides examples of navigation systems relating to bronchoscopy, it will be appreciated that the disclosed safety and data filtering aspects are applicable to other medical systems for navigation of a dynamic luminal network of a patient.

Various embodiments will be described below in conjunction with the drawings for purposes of illustration. It should be appreciated that many other implementations of the disclosed concepts are possible, and various advantages can be achieved with the disclosed implementations. Headings are included herein for reference and to aid in locating various sections. These headings are not intended to limit the scope of the concepts described with respect thereto. Such concepts may have applicability throughout the entire specification.

Overview of Example Navigation Systems

FIG. 1A illustrates an example operating environment 100 implementing one or more aspects of the disclosed navigation systems and techniques. The operating environment 100 includes patient 101, a platform 102 supporting the patient 101, a surgical robotic system 110 guiding movement of endoscope 115, command center 105 for controlling operations of the surgical robotic system 110, EM controller 135, EM field generator 120, and EM sensors 125, 130. FIG. 1A also illustrates an outline of a region of a luminal network 140 within the patient 101, shown in more detail in FIG. 1B.

The surgical robotic system 110 can include one or more robotic arms for positioning and guiding movement of endoscope 115 through the luminal network 140 of the patient 101. Command center 105 can be communicatively coupled to the surgical robotic system 110 for receiving position data and/or providing control signals from a user. As used herein, "communicatively coupled" refers to any wired and/or wireless data transfer mediums, including but not limited to a wireless wide area network (WWAN) (e.g., one or more cellular networks), a wireless local area network (WLAN) (e.g., configured for one or more standards, such as the IEEE 802.11 (Wi-Fi)), Bluetooth, data transfer cables, and/or the like. The surgical robotic system 110 is discussed in more detail with respect to FIG. 1C, and the command center 105 is discussed in more detail with respect to FIG. 2.

The endoscope 115 may be a tubular and flexible surgical instrument that is inserted into the anatomy of a patient to capture images of the anatomy (e.g., body tissue) and provide a working channel for insertion of other medical instruments to a target tissue site. In some implementations, the endoscope 115 can be a bronchoscope. The endoscope 115 can include one or more imaging devices (e.g., cameras or other types of optical sensors) at its distal end. The imaging devices may include one or more optical components such as an optical fiber, fiber array, photosensitive substrate, and/or lens(es). The optical components move along with the tip of the endoscope 115 such that movement of the tip of the endoscope 115 results in corresponding changes to the field of view of the images captured by the imaging devices. The distal end of the endoscope 115 can be provided with one or more EM sensors 125 for tracking the position of the distal end within an EM field generated around the luminal network 140. The distal end of the endoscope 115 is further described with reference to FIG. 3 below.

EM controller 135 can control EM field generator 120 to produce a varying EM field. The EM field can be time-varying and/or spatially varying, depending upon the embodiment. The EM field generator 120 can be an EM field generating board in some embodiments. Some embodiments of the disclosed patient navigation systems can use an EM field generator board positioned between the patient and the platform 102 supporting the patient, and the EM field generator board can incorporate a thin barrier that minimizes any tracking distortions caused by conductive or magnetic materials located below it. In other embodiments, an EM field generator board can be mounted on a robotic arm, for example similar to those shown in surgical robotic system 110, which can offer flexible setup options around the patient.

An EM spatial measurement system incorporated into the command center 105, surgical robotic system 110, and/or EM controller 135 can determine the location of objects within the EM field that are embedded or provided with EM sensor coils, for example EM sensors 125, 130. When an EM sensor is placed inside a controlled, varying EM field as described herein, voltages are induced in the sensor coils. These induced voltages can be used by the EM spatial measurement system to calculate the position and orientation of the EM sensor and thus the object having the EM sensor. As the magnetic fields are of a low field strength and can safely pass through human tissue, location measurement of an object is possible without the line-of-sight constraints of an optical spatial measurement system.

EM sensor 125 can be coupled to a distal end of the endoscope 115 in order to track its location within the EM field. The EM field is stationary relative to the EM field generator, and a coordinate frame of a 3D model of the luminal network can be mapped to a coordinate frame of the EM field. However, the patient's airways and thus the distal end of the endoscope 115 positioned within the airways can exhibit movement relative to the EM field generator 120 due to the respiratory cycles of the patient, leading to potential errors in determining the position of the distal end of the endoscope 115 relative to the model.

Accordingly, a number of additional EM sensors 130 can be provided on the body surface of the patient (e.g., in the region of the luminal network 140) in order to track displacement caused by respiration. A number of different EM sensors 130 can be spaced apart on the body surface in order to track the different displacements at these locations. For example, the periphery of the lungs may exhibit greater motion due to respiration than the central airways, and providing a number of EM sensors 130 as shown can enable more precise analysis of these motion effects. To illustrate, the distal end of the endoscope 115 travels through different regions of the luminal network 140 and thus experiences varying levels of displacement due to patient respiration as it travels through these different regions. The disclosed position filtering techniques can correlate the approximate position of the distal end of the endoscope 115 with one or more of the additional EM sensors 130, and can use identified displacement magnitudes of these specific additional EM sensors to correct for noise or artifacts in the endoscope position signal due to airway movement, for example, via filtering/removal of respiratory motion artifact component(s) of the endoscope position signal.

In other embodiments, other types of sensors configured to detect movement of the luminal network of the patient can be used instead of or in addition to the additional EM sensors 130. For example, one or more inertial sensors (e.g., accelerometer(s), gyroscope(s), etc.) can be positioned on the body surface of the patient to help estimate displacement of the chest surface during respiration. In another example, an acoustic respiratory sensor may be placed on the body surface of the patient in the region of the airways (e.g., luminal network region 140) and used to measure the inspiration and expiration phases of the respiration cycle. In another example, an optical sensor (e.g., an imaging device) can capture a stream of images of the patient's body and these images can be analyzed to identify respiration phase and/or displacement. In some implementations, the patient 101 may be breathing with assistance from a ventilator during the procedure, and the ventilator (and/or a device communicatively coupled to the ventilator) may provide data representing inspiration and expiration phases of the respiration cycle.

Figure 1B:
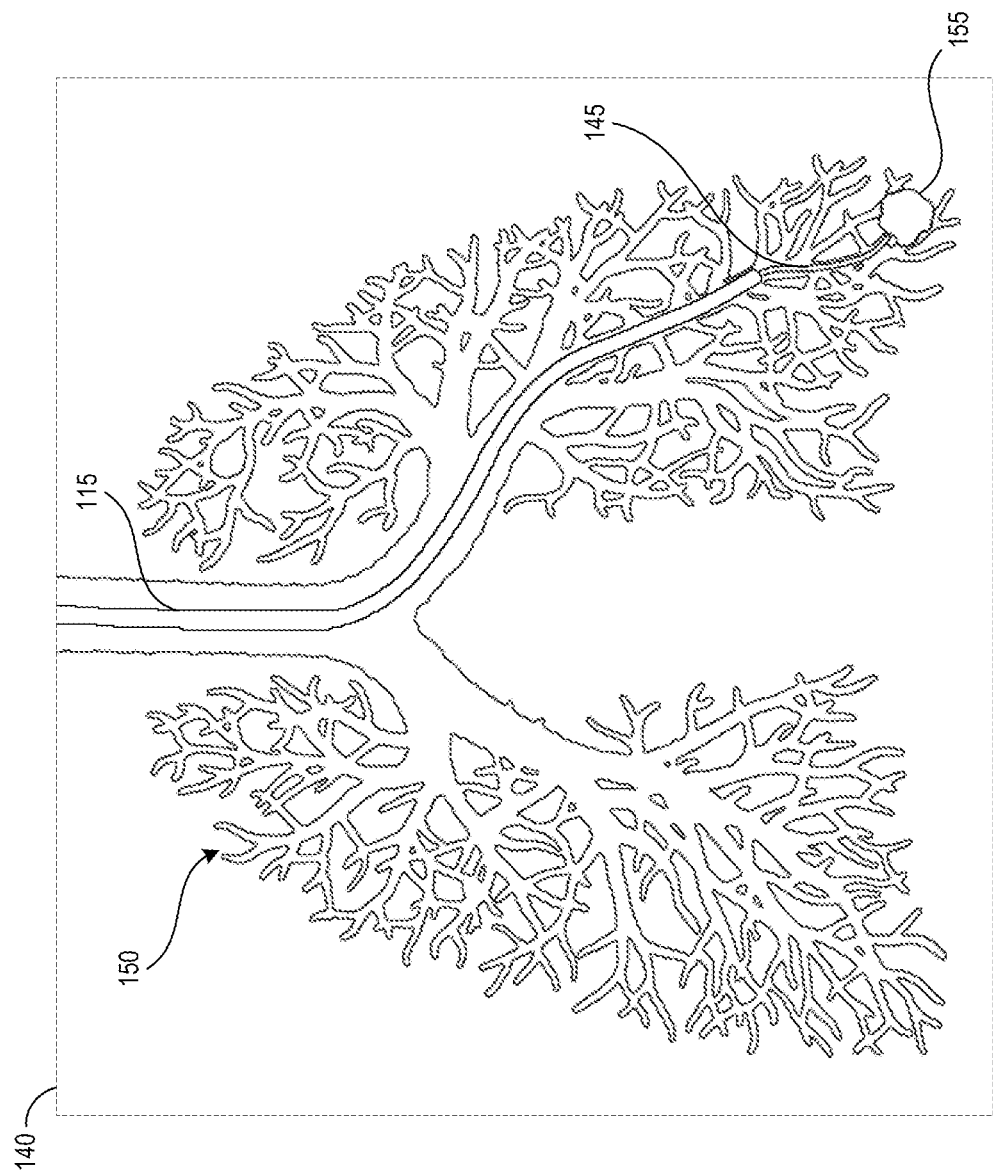
FIG. 1B illustrates an example luminal network navigated in the environment of FIG. 1A.

FIG. 1B illustrates an example luminal network 140 that can be navigated in the operating environment 100 of FIG. 1A. The luminal network 140 includes the branched structure of the airways 150 of the patient and a lesion 155 that can be accessed as described herein for diagnosis and/or treatment. As illustrated, the lesion 155 is located at the periphery of the airways 150. The endoscope 115 has a first diameter and thus its distal end is not able to be positioned through the smaller-diameter airways around the lesion 155.

Accordingly, a steerable catheter 155 extends from the working channel of the endoscope 115 the remaining distance to the lesion 155. The steerable catheter 145 may have a lumen through which instruments, for example biopsy needles, cytology brushes, and/or tissue sampling forceps, can be passed to the target tissue site of lesion 155. In such implementations, both the distal end of the endoscope 115 and the distal end of the steerable catheter 145 can be provided with EM sensors for tracking their position within the airways 150. In other embodiments, the overall diameter of the endoscope 115 may be small enough to reach the periphery without the steerable catheter 155, or may be small enough to get close to the periphery (e.g., within 2.5-3 cm) to deploy medical instruments through a non-steerable catheter. The medical instruments deployed through the endoscope 115 may be equipped with EM sensors, and the position filtering and safety-mode navigation techniques described below can be applied to such medical instruments.

In some embodiments, a 2D display of a 3D luminal network model as described herein, or a cross-section of a 3D model, can resemble FIG. 1B. Navigation safety zones and/or navigation path information can be overlaid onto such a representation.

Figure 1C:
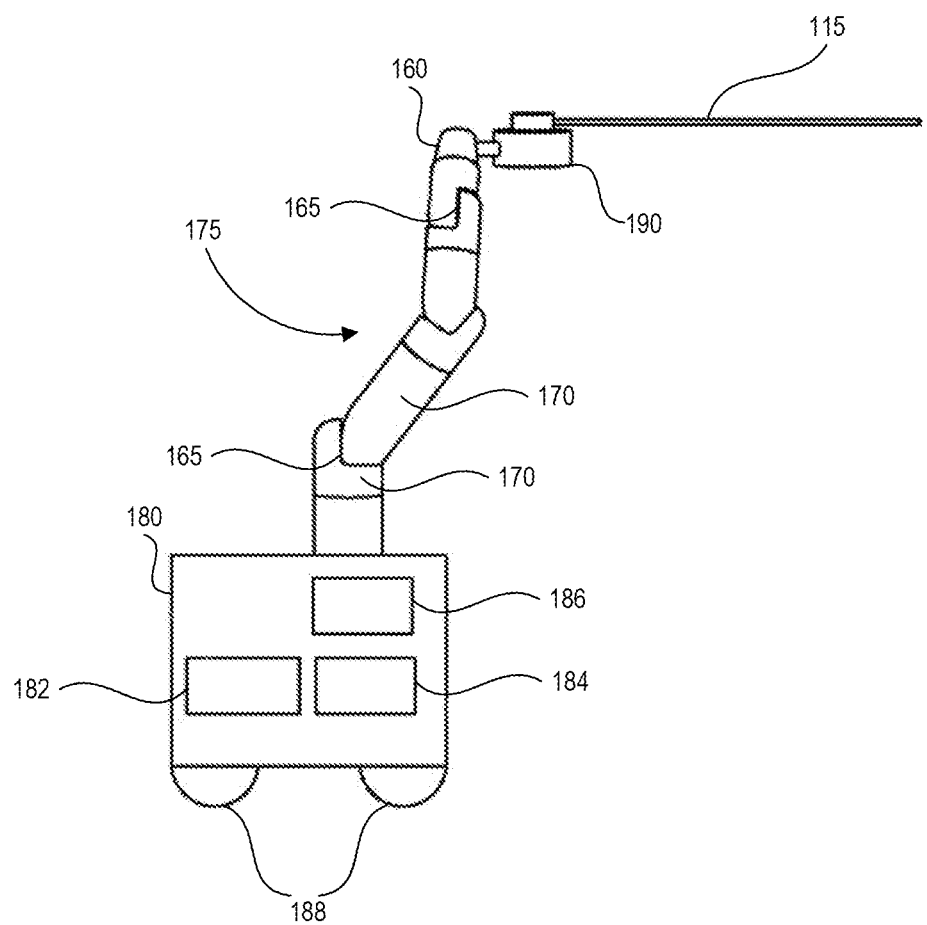
FIG. 1C illustrates an example robotic arm for guiding instrument movement in through the luminal network of FIG. 1B.

FIG. 1C illustrates an example robotic arm 175 of a surgical robotic system 110 for guiding instrument movement in through the luminal network 140 of FIG. 1B. The surgical robotic system 110 includes a base 180 coupled to one or more robotic arms, e.g., robotic arm 175. The robotic arm 175 includes multiple arm segments 170 coupled at joints 165, which provides the robotic arm 175 multiple degrees of freedom. As an example, one implementation of the robotic arm 175 can have seven degrees of freedom corresponding to seven arm segments. In some embodiments, the robotic arm 175 includes set up joints that use a combination of brakes and counter-balances to maintain a position of the robotic arm 175. The counter-balances may include gas springs or coil springs. The brakes, e.g., fail safe brakes, may be include mechanical and/or electrical components. Further, the robotic arm 175 may be gravity-assisted passive support type robotic arm.

The robotic arm 175 may be coupled to an instrument device manipulator (IDM) 190 using a mechanism changer interface (MCI) 160. The IDM 190 can be removed and replaced with a different type of IDM, for example, a first type of IDM configured to manipulate an endoscope or a second type of IDM configured to manipulate a laparoscope. The MCI 160 includes connectors to transfer pneumatic pressure, electrical power, electrical signals, and optical signals from the robotic arm 175 to the IDM 190. The MCI 160 can be a set screw or base plate connector. The IDM 190 manipulates surgical instruments, for example the endoscope 115 using techniques including direct drive, harmonic drive, geared drives, belts and pulleys, magnetic drives, and the like. The MCI 160 is interchangeable based on the type of IDM 190 and can be customized for a certain type of surgical procedure. The robotic 175 arm can include a joint level torque sensing and a wrist at a distal end.

Robotic arm 175 of the surgical robotic system 110 can manipulate the endoscope 115 using elongate movement members. The elongate movement members may include pull wires, also referred to as pull or push wires, cables, fibers, or flexible shafts. For example, the robotic arm 175 can actuate multiple pull wires coupled to the endoscope 115 to deflect the tip of the endoscope 115. The pull wires may include both metallic and non-metallic materials, for example stainless steel, Kevlar, tungsten, carbon fiber, and the like. The endoscope 115 may exhibit nonlinear behavior in response to forces applied by the elongate movement members. The nonlinear behavior may be based on stiffness and compressibility of the endoscope 115, as well as variability in slack or stiffness between different elongate movement members.

The base 180 can be positioned such that the robotic arm 175 has access to perform or assist with a surgical procedure on a patient, while a user such as a physician may control the surgical robotic system 110 from the comfort of the command console. In some embodiments, the base 180 may be coupled to a surgical operating table or bed for supporting the patient. The base 180 can be communicatively coupled to the command console 105 shown in FIG. 1A.

The base 180 can include a source of power 182, pneumatic pressure 186, and control and sensor electronics 184—including components such as a central processing unit, data bus, control circuitry, and memory—and related actuators such as motors to move the robotic arm 175. The electronics 184 can implement the navigation control techniques, safety modes, and/or data filtering techniques described herein. The electronics 184 in the base 180 may also process and transmit control signals communicated from the command console. In some embodiments, the base 180 includes wheels 188 to transport the surgical robotic system 110 and wheel locks/brakes (not shown) for the wheels 188. Mobility of the surgical robotic system 110 helps accommodate space constraints in a surgical operating room as well as facilitate appropriate positioning and movement of surgical equipment. Further, the mobility allows the robotic arm 175 to be configured such that the robotic arm 175 does not interfere with the patient, physician, anesthesiologist, or any other equipment. During procedures, a user may control the robotic arm 175 using control devices, for example the command console.

Figure 2:
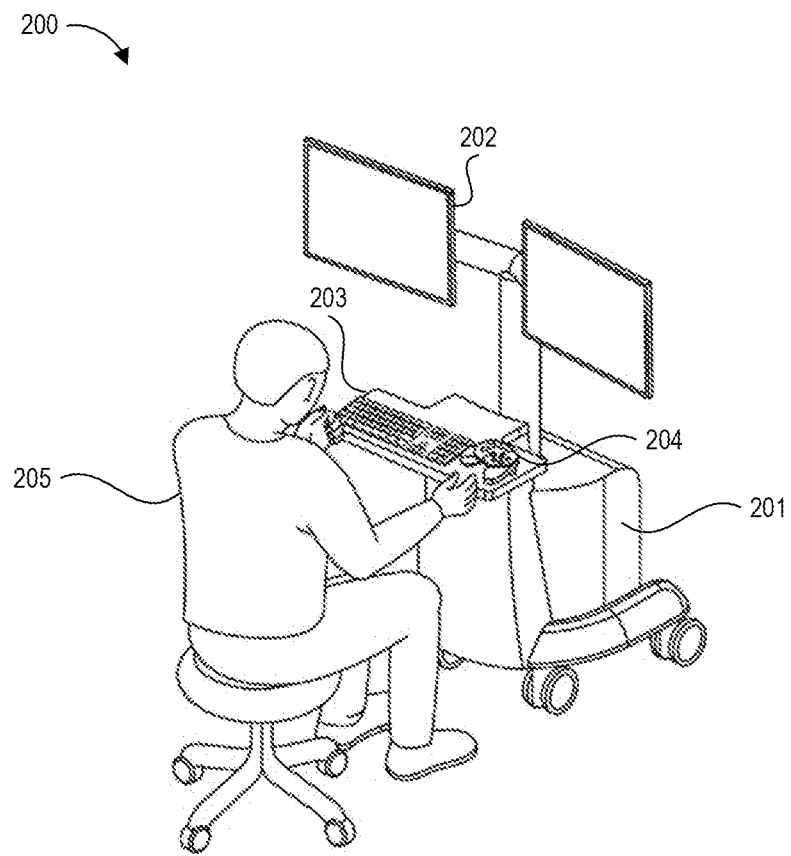
FIG. 2 illustrates an example command console for the example surgical robotic system, according to one embodiment.

FIG. 2 illustrates an example command console 200 that can be used, for example, as the command console 105 in the example operating environment 100. The command console 200 includes a console base 201, display modules 202, e.g., monitors, and control modules, e.g., a keyboard 203 and joystick 204. In some embodiments, one or more of the command console 200 functionality may be integrated into a base 180 of the surgical robotic system 110 or another system communicatively coupled to the surgical robotic system 110. A user 205, e.g., a physician, remotely controls the surgical robotic system 110 from an ergonomic position using the command console 200.

The console base 201 may include a central processing unit, a memory unit, a data bus, and associated data communication ports that are responsible for interpreting and processing signals such as camera imagery and tracking sensor data, e.g., from the endoscope 115 shown in FIGS. 1A-1C. In some embodiments, both the console base 201 and the base 180 perform signal processing for load-balancing. The console base 201 may also process commands and instructions provided by the user 205 through the control modules 203 and 204. In addition to the keyboard 203 and joystick 204 shown in FIG. 2, the control modules may include other devices, for example, computer mice, trackpads, trackballs, control pads, controllers such as handheld remote controllers, and sensors (e.g., motion sensors or cameras) that capture hand gestures and finger gestures. A controller can include a set of user inputs (e.g., buttons, joysticks, directional pads, etc.) mapped to an operation of the instrument (e.g., articulation, driving, water irrigation, etc.).

The user 205 can control a surgical instrument such as the endoscope 115 using the command console 200 in a velocity mode or position control mode. In velocity mode, the user 205 directly controls pitch and yaw motion of a distal end of the endoscope 115 based on direct manual control using the control modules. For example, movement on the joystick 204 may be mapped to yaw and pitch movement in the distal end of the endoscope 115. The joystick 204 can provide haptic feedback to the user 205. For example, the joystick 204 may vibrate to indicate that the endoscope 115 cannot further translate or rotate in a certain direction. The command console 200 can also provide visual feedback (e.g., pop-up messages) and/or audio feedback (e.g., beeping) to indicate that the endoscope 115 has reached maximum translation or rotation. The haptic and/or visual feedback can also be provided due to the system operating in a safety mode during patient expiration as described in more detail below.

In position control mode, the command console 200 uses a three-dimensional (3D) map of a patient luminal network and input from navigational sensors as described herein to control a surgical instrument, e.g., the endoscope 115. The command console 200 provides control signals to robotic arms 175 of the surgical robotic system 110 to manipulate the endoscope 115 to a target location. Due to the reliance on the 3D map, position control mode may require accurate mapping of the anatomy of the patient.

In some embodiments, users 205 can manually manipulate robotic arms 175 of the surgical robotic system 110 without using the command console 200. During setup in a surgical operating room, the users 205 may move the robotic arms 175, endoscope 115 (or endoscopes), and other surgical equipment to access a patient. The surgical robotic system 110 may rely on force feedback and inertia control from the users 205 to determine appropriate configuration of the robotic arms 175 and equipment.

The displays 202 may include electronic monitors (e.g., LCD displays, LED displays, touch-sensitive displays), virtual reality viewing devices, e.g., goggles or glasses, and/or other display devices. In some embodiments, the display modules 202 are integrated with the control modules, for example, as a tablet device with a touchscreen. In some embodiments, one of the displays 202 can display a 3D model of the patient's luminal network and virtual navigation information (e.g., a virtual representation of the end of the endoscope within the model based on EM sensor position) while the other of the displays 202 can display image information received from the camera or another sensing device at the end of the endoscope 115. In some implementations, the user 205 can both view data and input commands to the surgical robotic system 110 using the integrated displays 202 and control modules. The displays 202 can display 2D renderings of 3D images and/or 3D images using a stereoscopic device, e.g., a visor or goggles. The 3D images provide an "endo view" (i.e., endoscopic view), which is a computer 3D model illustrating the anatomy of a patient. The "endo view" provides a virtual environment of the patient's interior and an expected location of an endoscope 115 inside the patient. A user 205 compares the "endo view" model to actual images captured by a camera to help mentally orient and confirm that the endoscope 115 is in the correct—or approximately correct—location within the patient. The "endo view" provides information about anatomical structures, e.g., the shape of airways, circulatory vessels, or an intestine or colon of the patient, around the distal end of the endoscope 115. The display modules 202 can simultaneously display the 3D model and CT scans of the anatomy the around distal end of the endoscope 115.

Further, the display modules 202 may overlay the already determined navigation paths of the endoscope 115 on the 3D model and CT scans.

In some embodiments, a model of the endoscope 115 is displayed with the 3D models to help indicate a status of a surgical procedure. For example, the CT scans identify a lesion in the anatomy where a biopsy may be necessary. During operation, the display modules 202 may show a reference image captured by the endoscope 115 corresponding to the current location of the endoscope 115. The display modules 202 may automatically display different views of the model of the endoscope 115 depending on user settings and a particular surgical procedure. For example, the display modules 202 show an overhead fluoroscopic view of the endoscope 115 during a navigation step as the endoscope 115 approaches an operative region of a patient.

Figure 3:
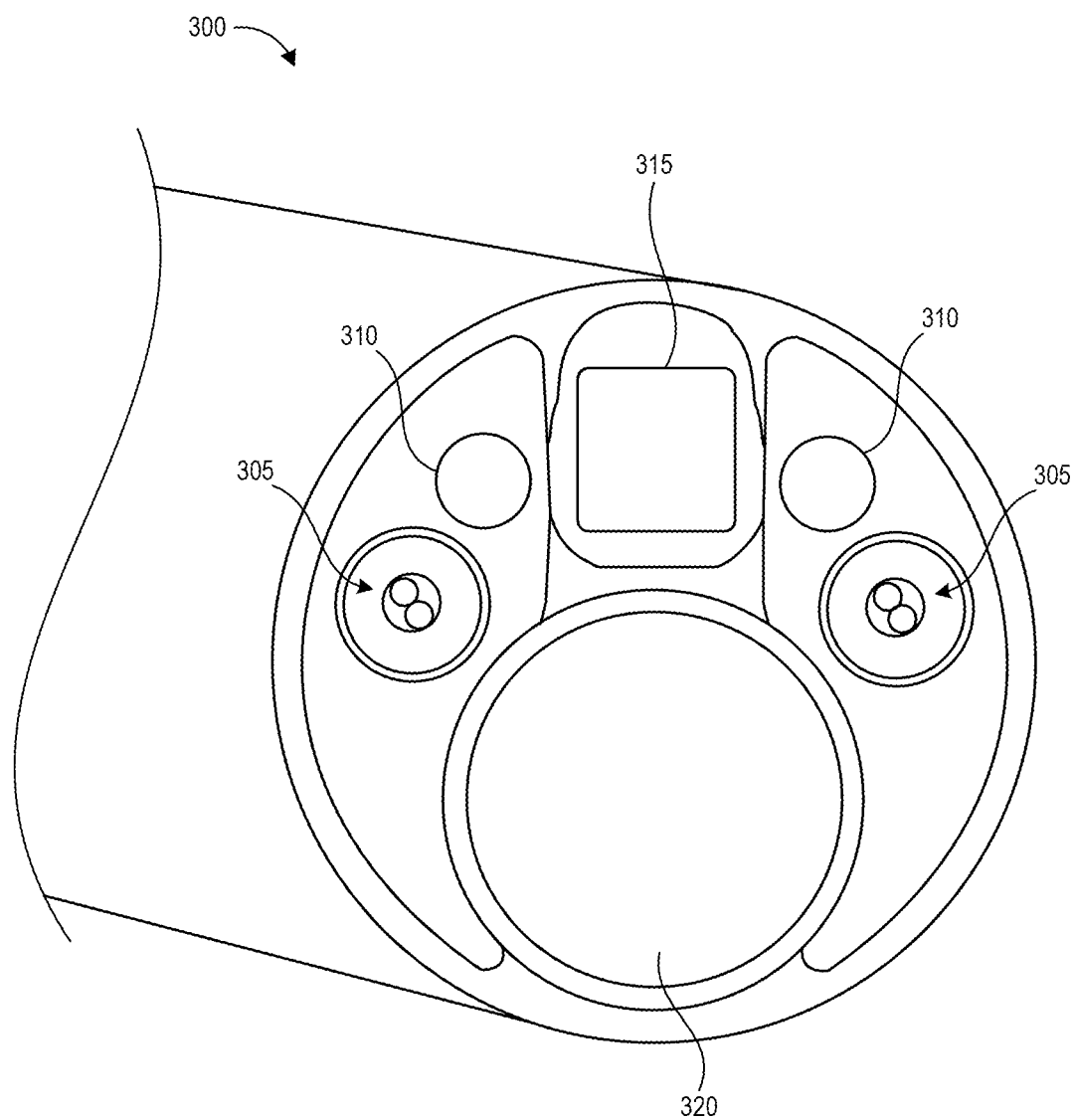
FIG. 3 illustrates an example endoscope having imaging and EM sensing capabilities as described herein.

FIG. 3 illustrates the distal end 300 of an example endoscope having imaging and EM sensing capabilities as described herein, for example the endoscope 115 of FIGS. 1A-1C. In FIG. 3, the distal end 300 of the endoscope includes an imaging device 315, illumination sources 310, and ends of EM sensor coils 305. The distal end 300 further includes an opening to a working channel 320 of the endoscope through which surgical instruments, such as biopsy needles, cytology brushes, and forceps, may be inserted along the endoscope shaft, allowing access to the area near the endoscope tip.

The illumination sources 310 provide light to illuminate a portion of an anatomical space. The illumination sources can each be one or more light-emitting devices configured to emit light at a selected wavelength or range of wavelengths. The wavelengths can be any suitable wavelength, for example visible spectrum light, infrared light, x-ray (e.g., for fluoroscopy), to name a few examples. In some embodiments, illumination sources 310 can include light-emitting diodes (LEDs) located at the distal end 300. In some embodiments, illumination sources 310 can include one or more fiber optic fibers extending through a length of the endoscope to transmit light through the distal end 300 from a remote light source, for example an x-ray generator. Where the distal end 300 includes multiple illumination sources 310 these can each be configured to emit the same or different wavelengths of light as one another.

The imaging device 315 can include any photosensitive substrate or structure configured to convert energy representing received light into electric signals, for example a charge-coupled device (CCD) or complementary metal-oxide semiconductor (CMOS) image sensor. Some examples of imaging device 315 can include one or more optical fibers, for example a fiber optic bundle, configured to transmit an image from the distal end 300 of the endoscope to an eyepiece and/or image sensor at the proximal end of the endoscope. Imaging device 315 can additionally include one or more lenses and/or wavelength pass or cutoff filters as required for various optical designs. The light emitted from the illumination sources 310 allows the imaging device 315 to capture images of the interior of a patient's luminal network. These images can then be transmitted as individual frames or series of successive frames (e.g., a video) to a computer system such as command console 200 for processing as described herein.

Electromagnetic coils 305 located on the distal end 300 may be used with an electromagnetic tracking system to detect the position and orientation of the distal end 300 of the endoscope while it is disposed within an anatomical system. In some embodiments, the coils 305 may be angled to provide sensitivity to electromagnetic fields along different axes, giving the disclosed navigational systems the ability to measure a full 6 degrees of freedom: three positional and three angular. In other embodiments, only a single coil may be disposed on or within the distal end 300 with its axis oriented along the endoscope shaft of the endoscope. Due to the rotational symmetry of such a system, it is insensitive to roll about its axis, so only 5 degrees of freedom may be detected in such an implementation.

Figure 4:
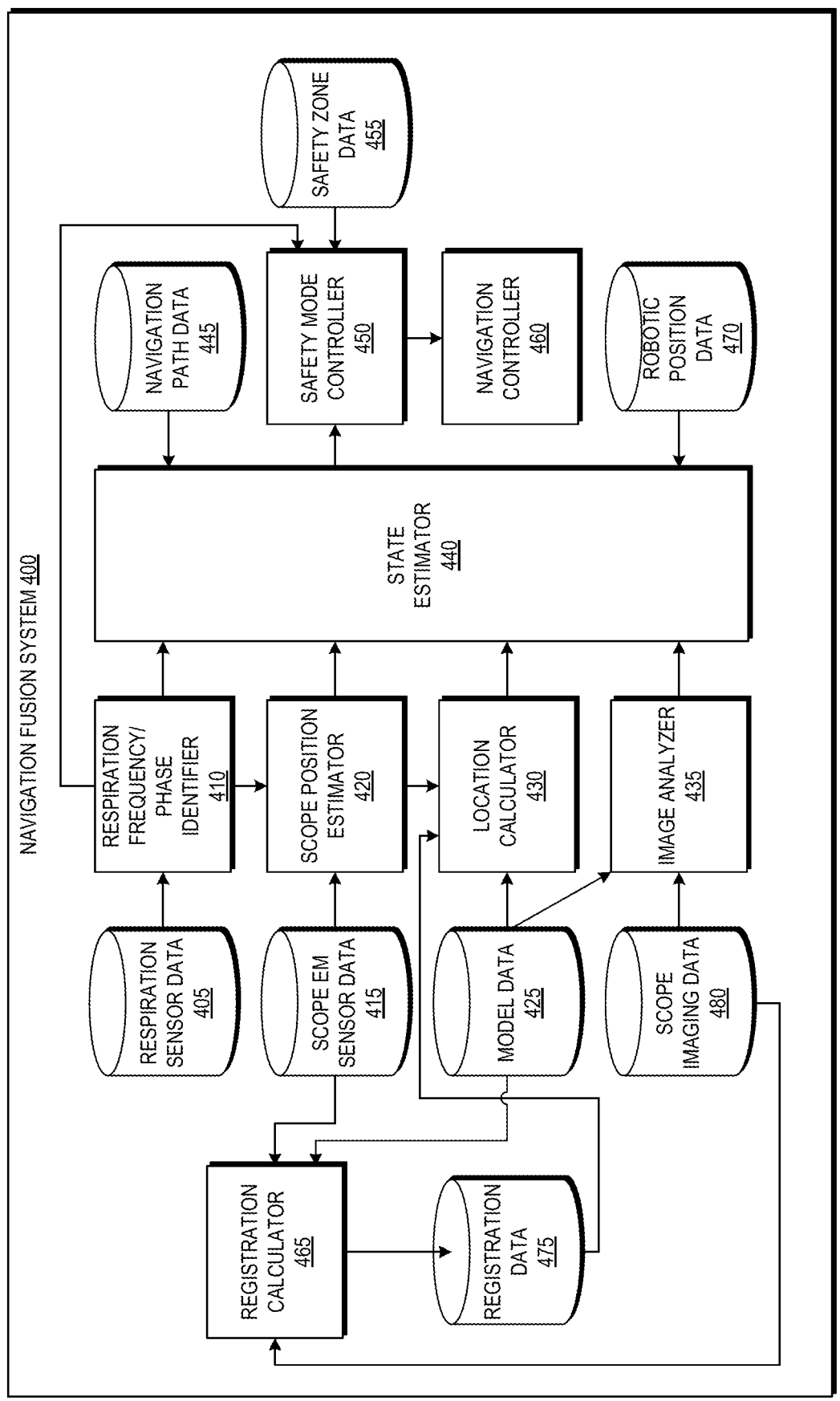
FIG. 4 depicts a schematic block diagram of a navigation system as described herein.

FIG. 4 illustrates a schematic block diagram of an example navigation fusion system 400 as described herein. As described in more detail below, using the framework 400, data from a number of different sources is combined and repeatedly analyzed during a surgical procedure to provide an estimation of the real-time movement information and location/orientation information of a surgical instrument (e.g., the endoscope) within the luminal network of the patient and to make navigation decisions. The system 400 includes a number of data repositories including respiration sensor data repository 405, endoscope EM sensor data repository 415, registration data repository 475, model data repository 425, endoscope imaging data repository 480, navigation path data repository 445, safety zone data repository 455, and robotic position data repository 470. Though shown separately in FIG. 4 for purposes of clarity in the discussion below, it will be appreciated that some or all of the data repositories can be stored together in a single memory or set of memories. The system 400 also includes a number of processing modules including respiration frequency and/or phase identifier 410, endoscope position estimator 420, registration calculator 465, location calculator 430, image analyzer 435, state estimator 440, safety mode controller 450, and navigation controller 460. Each module can represent a set of computer-readable instructions, stored in a memory, and one or more processors configured by the instructions for performing the features described below together. The navigation fusion system 400 can be implemented as one or more data storage devices and one or more hardware processors, for example in the control and sensor electronics 184 and/or console base 201 described above.

Respiration sensor data repository 405 is a data storage device that stores data derived from a respiration sensor. As described above, the respiratory sensor can comprise EM sensor(s) 130, an acoustic respiratory sensor, an image sensor having a field of view positioned to capture images of the luminal network, and ventilator inflation/deflation information. In some embodiments, the respiratory sensor can comprise a number of EM sensors 130 and the data in the respiration sensor data repository 405 can include, for each sensor, time-dependent position data representing the positions of the sensor in the EM field over time. For example, data for each sensor can be stored as a tuple in the form of (x, y, z, $t_n$) where x, y, and z represent the coordinates of the sensor in the EM field at time $t_n$. The respiration sensor data repository 405 can store a number of such tuples for each sensor corresponding to a number of different times.

The respiration frequency and/or phase identifier 410 is a module configured to receive data from the respiration sensor data repository 405 and analyze such data to calculate the frequency and/or phase of respiration. Frequency refers to the time interval between successive phases, for example between successive cycles of inspiration and expiration. Phase refers to whether the respiration cycle is an inspiration phase (e.g., while the patient is inhaling) or an expiration phase (e.g., while the patient is exhaling). Some embodiments can use a Fourier transform to extract the frequency of respiration from the respiration sensor data, using data from one or all of the sensors in various embodiments.

The endoscope EM sensor data repository 415 is a data storage device that stores data derived from an EM sensor at the distal end of an endoscope. As described above, such a sensor could include EM sensor 125, and EM sensor coils 305 and the resulting data can be used to identify position and orientation of the sensor within the EM field. Similar to the data from EM respiration sensors, data for an endoscope EM sensor can be stored as a tuple in the form of (x, y, z, $t_n$) where x, y, and z represent the coordinates of the sensor in the EM field at time $t_n$. Some embodiments may further include roll, pitch, and yaw of the instrument in the EM sensor tuple. The endoscope EM sensor data repository 415 can store a number of such tuples for each endoscope-based sensor corresponding to a number of different times.

The endoscope position estimator 420 is a module that receives data from the endoscope EM sensor data repository 415 and additionally from the respiration frequency and/or phase identifier 410 in some embodiments, and to use such data to reduce "noise" in the signal received from the endoscope EM sensor due to cyclic movement of the luminal network of the patient. For example, in one implementation endoscope position estimator 420 can generate a filter based on the determined respiration frequency and apply the filter to the data from the endoscope EM sensor. In another implementation, endoscope position estimator 420 can identify a magnitude of displacement of one or more of the respiration sensors during respiration and can apply the displacement value as a bias to the position indicated by the endoscope EM sensor data. This can be performed dynamically, for example by identifying respiration sensor displacement at time $t_n$ and applying that as a bias to the endoscope position at time $t_n$, by identifying a next respiration sensor displacement at time $t_{n+1}$ and applying that as a bias to the endoscope position at time $t_{n+1}$, and so on.

The model data repository 425 is a data storage device that stores data representing a model of the luminal network of the patient. As an example, a preoperative procedure can be performed to take CT scans of a patient's lungs, and a computing system can use data from these scans to build a 3D model of the lungs of the patient. Such a model can provide 3D information about the structure and connectivity of the luminal network, including the topography and/or diameters of patient airways in some examples. Some CT scans are performed at breath-hold so that the patient's airways are expanded to their full diameter.

The registration calculator 465 is a module that can identify a registration or mapping between the coordinate frame of the 3D model (e.g., a coordinate frame of the CT scanner used to generate the model) and the coordinate frame of the EM field (e.g., of the EM field generator 120). In order to track a sensor through the patient's anatomy, the navigation fusion system 400 may require a process known as "registration," by which the registration calculator 465 finds the geometric transformation that aligns a single object between different coordinate systems. For instance, a specific anatomical site on a patient may have a representation in the 3D model coordinates and also in the EM sensor coordinates. In order to calculate an initial registration, one implementation of the registration calculator 465 can perform registration as described in U.S. application Ser. No. 15/268,238, filed Sep. 17, 2016, titled "Navigation of Tubular Networks," the disclosure of which is hereby incorporated by reference. As an example of one possible registration technique, the registration calculator 465 can receive data from the endoscope imaging data repository 480 and the EM sensor data repository 415 at a number of different points as the endoscope is inserted into the airways of the patient, for example as the endoscope reaches various bifurcations. The image data can be used to identify when the distal end of the endoscope has reached a bifurcation, for example via automated feature analysis. The registration calculator 465 can receive data from the endoscope EM sensor data repository 415 and identify a location of the EM sensor at the distal end of the endoscope as the endoscope is positioned at the bifurcation. Some examples can use not only bifurcations but other points in the patient's airway, and may map such points to corresponding points in a "skeleton" model of the airway. The registration calculator 465 can can use data linking at least three of EM positions to points in the model in order to identify the geometric transformation between the EM field and the model. Another embodiment can involve manual registration, for example by taking at least 3 from a first bifurcation of the patient's airway and from two more bifurcations in the left and right lungs, and can use the corresponding points to calculate the registration. This data to perform the geometric transformation (also referred to as registration data) can be stored in the registration data repository 475 as registration data.

After the initial registration is determined, the registration calculator 465 may update its estimate of the registration transform based on received data so as to increase transform accuracy as well as to compensate for changes to the navigation system, e.g., changes due to movement of the patient. In some aspects, the registration calculator 465 may update the estimate of the registration transform continually, at defined intervals, and/or based on the position of the endoscope (or component(s) thereof) in the luminal network.

Registration data repository 475 is a data storage device that stores the registration data that, as just discussed, is usable to perform a geometric transformation from the coordinate frame of the EM field to the coordinate frame of the model. Also discussed above, the registration data may be generated by the registration calculator 465 and may be updated continually or periodically in some implementations.

The location calculator 430 is a module that receives data from the model data repository 425, registration data repository 475, and the scope position estimator 420 to translate EM sensor coordinates into 3D model coordinates. The scope position estimator 420 calculates an initial position of the EM sensor relative to the position of the EM field generator, as described above. This position also corresponds to a location within the 3D model. In order to translate the initial position of the EM sensor from the EM coordinate frame into the model coordinate frame, the location calculator 430 can access the mapping between the EM coordinate frame and the model coordinate frame (e.g., registration data) as stored in the registration data repository 475. In order to translate the scope position into the 3D model coordinate frame, the location calculator 430 receives, as input, data representing the topography of the 3D model from the model data repository 425, data representing the registration between the EM field and the coordinate frame of the 3D model from the registration data repository 475, and the position of the scope in the EM field from the scope position estimator 420. Some embodiments can also receive prior estimated state data from the state estimator 440. Based on the received data, the location calculator 430 may perform, e.g., on-the-fly transformation of the EM sensor position data to a position in the 3D model. This can represent a preliminary estimate of the position of the distal end of the scope within the topography of the 3D model and can be provided as one input to the state estimator 440 for generating a final estimate of the scope position, as described in more detail below.

The endoscope imaging data repository 480 is a data storage device that stores image data received from a camera of the endoscope, for example the imaging device 315. The image data can be discrete images or series of image frames in a video sequence in various embodiments.

The image analyzer 435 is a module that receives data from the endoscope imaging data repository 480 and model data repository 425 and can compare this data to determine endoscope positioning. For example, the image analyzer 435 can access volume-rendered or surface-rendered endoluminal images of the airway tree from the model scans and can compare the rendered images with the real-time image or video frames from the imaging device 315. For example, the images can be registered (e.g., using Powell's optimization, simplex or gradient methods, gradient descent algorithms with normalized cross correlation or mutual information as costs), and then weighted normalized sum of square difference errors and normalized mutual information can be used for comparing the registered images obtained from the two sources. Similarity between a 2D image from the scan and a 2D image received from the endoscope can indicate that the endoscope is positioned near the location of the image from the scan. Such image-based navigation can perform local registrations at bifurcations of patient airways and so can be less susceptible to noise due to patient breathing motion than EM tracking systems. However, as the image analyzer 435 relies on the endoscope video, the analysis can be affected by artifacts in the images caused by patient coughing or mucous obstruction.

The image analyzer 435 can implement object recognition techniques in some embodiments, by which the image analyzer 435 can detect objects present in the field of view of the image data, such as branch openings, lesions, or particles. Using object recognition, the image analyzer can output object data indicating information about what objects were identified, as well as positions, orientations, and/or sizes of objects represented as probabilities. As one example, object recognition can be used to detect objects that may indicate branch points in a luminal network and then determine their position, size, and/or orientation. In one embodiment, in a given image within a luminal network, each branch will typically appear as a dark, approximately elliptical region, and these regions may be detected automatically by a processor, using region-detection algorithms such as maximally stable extremal regions (MSER) as objects. The image analyzer 435 can use light reflective intensity combined with other techniques to identify airways. Further, image analyzer 435 can further track detected objects across a set of sequential image frames to detect which branch has been entered from among a set of possible branches in the luminal network.

The robotic position data repository 470 is a data storage device that stores robotic position data received from surgical robotic system 110, for example data related to physical movement of the medical instrument or part of the medical instrument (e.g., the instrument tip or distal end) by the surgical robotic system 110 within the luminal network. Example robotic position data may include, e.g., command data instructing the instrument tip to reach a specific anatomical site and/or change its orientation (e.g., with a specific pitch, roll, yaw, insertion, and retraction for one or both of a leader and a sheath of an endoscopic instrument) within the luminal network, insertion data representing insertion movement of the part of the medical instrument (e.g., the instrument tip or sheath), IDM data, and mechanical data representing mechanical movement of an elongate member of the medical instrument, such as, for example, motion of one or more pull wires, tendons or shafts of the endoscope that drive the actual movement of the endoscope within the luminal network.

The navigation path data repository 445 is a data storage device that stores data representing a pre-planned navigation path through the luminal network to a target tissue site. Navigating to a particular point in a luminal network of a patient's body may require certain steps to be taken pre-operatively in order to generate the information needed to create the 3D model of the tubular network and to determine a navigation path within it. As described above, a 3D model may be generated of the topography and structure of the specific patient's airways. A target can be selected, for example a lesion to biopsy or a portion of organ tissue to repair surgically. In one embodiment, the user is capable of selecting the location of the target by interfacing with a computer display that can show the 3D model, such as by clicking with a mouse or touching a touchscreen. In some embodiments, the navigation path may be identified programmatically by analysis of the model and an identified lesion site to derive a shortest navigation path to the lesion. In some embodiments the path may be identified by a physician, or an automatically-identified path may be modified by a physician. The navigation path can identify a sequence of branches within the luminal network to travel through so as to reach the identified target.

The state estimator 440 is a module that receives inputs and performs analysis of the inputs to determine a state of the medical instrument. For example, the state estimator 440 can receive, as inputs, data from the respiration frequency and/or phase identifier 410, scope position estimator 420, location calculator 430, image analyzer 435, navigation path data repository 445, and robotic position data repository 470. The state estimator 440 can implement a probabilistic analysis to determine a state and corresponding probability of the medical instrument within the luminal network given the provided inputs. Estimated state can refer to one or more of (1) the x,y,z position of the instrument relative to a coordinate frame of a model of the luminal network, (2) whether the instrument is located in a certain region of the model, for example a particular airway branch or pre-identified safety zone, (3) pitch, roll, yaw, insertion, and/or retraction of the instrument, and (4) distance to target. The state estimator 440 can provide the estimated state of the instrument (or the distal tip of the instrument) as a function of time.

In some embodiments, the state estimator 440 can implement a Bayesian framework to determine the state and corresponding probability. Bayesian statistical analysis starts with a belief, called a prior, and then update that belief with observed data. The prior represents an estimate of what the Bayesian model parameters might be and can be represented as a parameterized distribution. The observed data can be gathered to obtain evidence about actual values of the parameters. The outcome of Bayesian analysis is called a posterior, and represents a probabilistic distribution expressing events in terms of confidence. If further data is obtained the posterior can be treated as the prior and updated with the new data. This process employs the Bayes rule, which indicates a conditional probability, for example how likely is event A if event B happens.

With respect to the disclosed navigation fusion system 400, the state estimator 440 can use previously estimated state data as the prior and can use the inputs from the respiration frequency and/or phase identifier 410, scope position estimator 420, location calculator 430, image analyzer 435, navigation path data repository 445, and/or robotic position data repository 470 as observed data. At the outset of a procedure, a vision-based initialization technique can be used to estimate the initial depth and roll in the trachea, and this estimate can be used as the prior. The state estimator 440 can perform Bayesian statistical analysis of the prior and observed data to generate a posterior distribution representing a probability and confidence value of each of a number of possible states.

The "probability" of the "probability distribution", as used herein, refers to a likelihood of an estimation of a possible location and/or orientation of the medical instrument being correct. For example, different probabilities may be calculated by one of the algorithm modules indicating the relative likelihood that the medical instrument is in one of several different possible branches within the luminal network. In one embodiment, the type of probability distribution (e.g., discrete distribution or continuous distribution) is chosen to match features of an estimated state (e.g., type of the estimated state, for example continuous position information vs. discrete branch choice). As one example, estimated states for identifying which segment the medical instrument is in for a trifurcation may be represented by a discrete probability distribution, and may include three discrete values of 20%, 30% and 50% representing chance as being in the location inside each of the three branches as determined by one of the algorithm modules. As another example, the estimated state may include a roll angle of the medical instrument of 40±5 degrees and a segment depth of the instrument tip within a branch may be is 4±1 mm, each represented by a Gaussian distribution which is a type of continuous probability distribution.

In contrast, the "confidence value," as used herein, reflects a measure of confidence in the estimation of the state provided by one of the modules of FIG. 4 based one or more factors. For the EM-based modules, factors such as distortion to EM Field, inaccuracy in EM registration, shift or movement of the patient, and respiration of the patient may affect the confidence in estimation of the state. Particularly, the confidence value in estimation of the state provided by the EM-based modules may depend on the particular respiration cycle of the patient, movement of the patient or the EM field generators, and the location within the anatomy where the instrument tip locates. For the image analyzer 435, examples factors that may affect the confidence value in estimation of the state include illumination condition for the location within the anatomy where the images are captured, presence of fluid, tissue, or other obstructions against or in front of the optical sensor capturing the images, respiration of the patient, condition of the tubular network of the patient itself (e.g., lung) such as the general fluid inside the tubular network and occlusion of the tubular network, and specific operating techniques used in, e.g., navigating or image capturing.

For example one factor may be that a particular algorithm has differing levels of accuracy at different depths in a patient's lungs, such that relatively close to the airway opening, a particular algorithm may have a high confidence in its estimations of medical instrument location and orientation, but the further into the bottom of the lung the medical instrument travels that confidence value may drop. Generally, the confidence value is based on one or more systemic factors relating to the process by which a result is determined, whereas probability is a relative measure that arises when trying to determine the correct result from multiple possibilities with a single algorithm based on underlying data.

As one example, a mathematical equation for calculating results of an estimated state represented by a discrete probability distribution (e.g., branch/segment identification for a trifurcation with three values of an estimated state involved) can be as follows:

$$S_1 = C_{EM}*P_{1,EM} + C_{Image}*P_{1,Image} + C_{Robot}*P_{1,Robot};$$

$$S_2 = C_{EM}*P_{2,EM} + C_{Image}*P_{2,Image} + C_{Robot}*P_{2,Robot};$$

$$S_3 = C_{EM}*P_{3,EM} + C_{Image}*P_{3,Image} + C_{Robot}*P_{3,Robot}$$

In the example mathematical equation above, $S_i(i=1, 2, 3)$ represents possible example values of an estimated state in a case where 3 possible segments are identified or present in the 3D model, $C_{EM}$, $C_{Image}$, and $C_{Robot}$ represents confidence value corresponding to EM-based algorithm, image-based algorithm, and robot-based algorithm and $P_{i,EM}$, $P_{i,image}$, and $P_{i,Robot}$ represent the probabilities for segment i. Because of the probabilistic nature of such a fusion algorithm, respiration can be tracked over time and even predicted to overcome latency and outlier disturbances.

In some embodiments, confidence values for data from the scope position estimator 420, registration calculator, and image analyzer 435 can be adaptively determined based on the respiration phase from the respiration frequency and/or phase identifier 410. For example, robotic position data and image data can be affected differently than EM sensor data by respiration motion. In some embodiments, vision data obtained from the endoscope imaging data repository 430 can be used to detect certain kinds of respiratory motion that are not detectable via sensors external to the luminal network, for example movement of an airway in a cranial-caudal (backward-forward) motion that can be detected through vision processing.

The safety zone data repository 455 is a data storage device that stores data representing areas and/or conditions for which particular caution should be exercised during instrument insertion. For example, as described above the 3D model can include information relating to airway diameter. Branches of the luminal network having diameters less than or equal to the diameter of the endoscope, or within a predetermined threshold (e.g., 1-2 mm, around 4 mm, or any other threshold distance) of the endoscope diameter, can be designated as safety zones. Such designation can be made programmatically by a processor in some embodiments via comparison of the diameters. As another example, certain phases of the patient respiration cycle can be designated as a safety "zone," such as the expiration phase of patient respiration, or such as a transition phase beginning in expiration and ending partway into inspiration during which the patient's airways are expected to be constricted. In some embodiments the threshold can be configurable based on factors including dimensions of the instrument, control tolerances of the controlled movement, user configurable preferences, etc. The safety zone data repository 455 can store instructions regarding robotic system operation and/or limitations in various safety zones in some embodiments.

The safety mode controller 450 is a module that receives a number of inputs and determine whether to activate a safety mode. For example, the safety mode controller 450 can receive, as inputs, data from the safety zone data repository 455, respiration phase data from the respiration frequency and/or phase identifier 410, and an estimated state output from the state estimator 440. The safety mode controller 450 can compare the respiration phase and estimated state to the data from the safety zone repository to determine whether to activate a safety mode.

The navigation controller 460 is a module that receives data from the safety mode controller 450 and uses this data to guide further operation of the surgical robotic system 110. For example, when a safety mode is activated, the navigation controller 460 can receive data from the safety mode controller 450 regarding specific display instructions and/or IDM operation instructions. When a safety mode is not activated, the navigation controller 460 can receive data from the safety mode controller 450 regarding the estimated state and any next movement identified in the navigation path data.

Overview of Example Navigation Techniques

Figure 5:
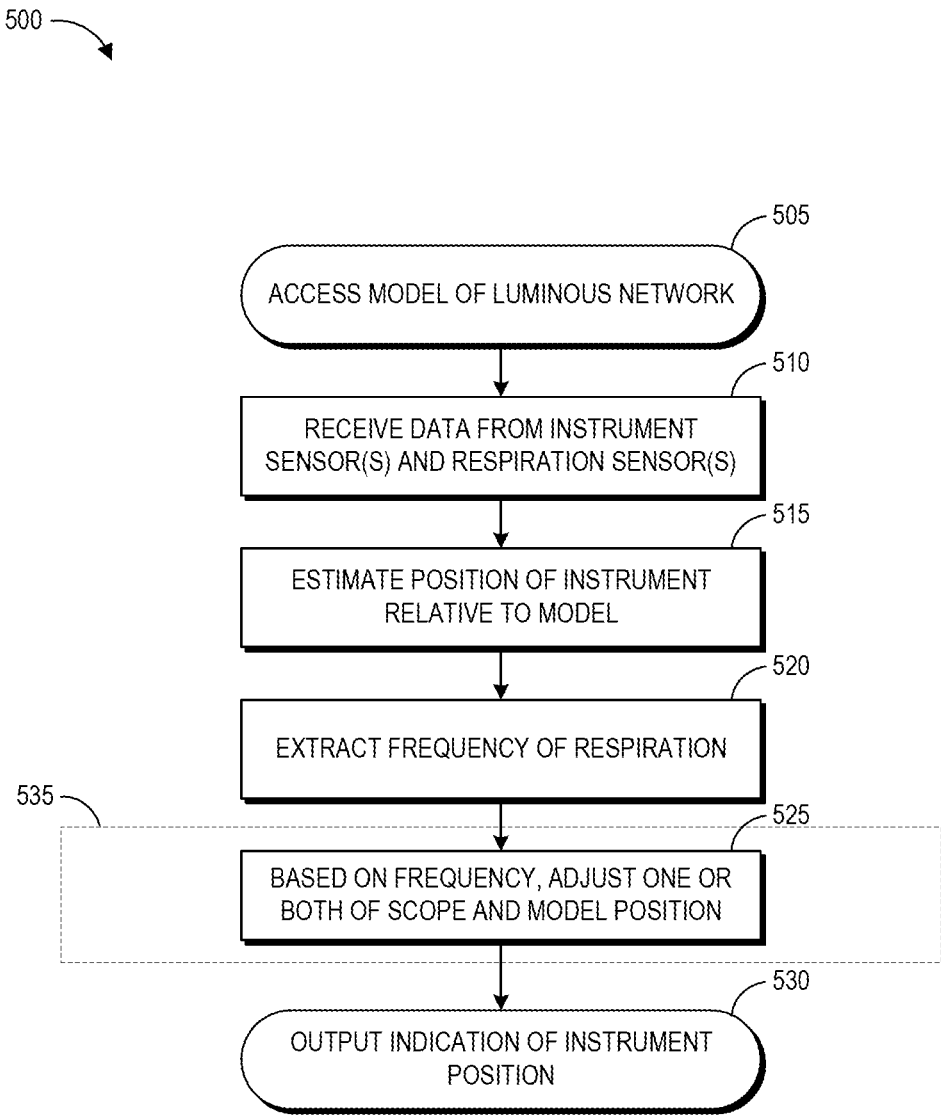
FIG. 5 depicts a flowchart of an example process for filtering noise due to luminal network movement from instrument position estimations as described herein.

In accordance with one or more aspects of the present disclosure, FIG. 5 depicts a flowchart of an example process 500 for filtering out noise due to luminal network movement from instrument position estimations as described herein. The process 500 can be implemented in the navigation fusion system 400 FIG. 4, the control and sensor electronics 184 of FIG. 1, and/or the console base 201 of FIG. 2, or component(s) thereof.

At block 505, location calculator 430 can access a model of a patient's luminal network, for example, from model data repository 425. For example, the model can be a segmented map of a patient's airways generated from CT scans in some implementations. The model can be any two or three dimensional representation of the actual luminal network (or a portion of the luminal network) of the patient.

At block 510, the endoscope position estimator 420 can receive data from instrument sensor(s) and the respiration frequency/phase identifier 410 can receive data respiration sensor(s), for example from respiration sensor data repository 405 and endoscope EM sensor data repository 410, respectively. As described above, the endoscope sensor data can be derived from an EM sensor on an endoscope and can provide location and/or orientation of a distal end of the endoscope within an EM field generated around the luminal network, and the respiration sensor data can be generated by a sensor positioned to detect movement of the luminal network.

At block 515, the location calculator 430 can estimate a position of the instrument relative to the model. For example, a coordinate frame of the model may be mapped to a coordinate frame of the EM field at the outset of the medical procedure during registration (see above discussion on registration calculator 465 and registration data repository 475). The location calculator 430 can use this mapping (via the registration data) together with coordinates of the sensor position within the field to generate an initial estimate a location of the instrument sensor within the model. However, as described above, due to motion of patient airways during respiration, the initial registration of the model to the EM field coordinate frame may not accurately reflect the actual, dynamic position of the patient's airways within the EM field. Because the instrument is located within one of the dynamically moving airways, when the airway location within the EM field varies from the mapped location of that same airway in the model, the position estimated at block 515 may be inaccurate, e.g., to the respiratory motion artifact/component of the estimated position of the instrument.

At block 520, the respiration frequency and/or phase identifier 410 can extract the frequency of the respiration from the data from the respiration sensor(s), for example by using a Fourier transform to extract the frequency of the respiration. The Fourier transform can be applied to data from one or more sensors in embodiments having multiple respiration sensors.

At block 525, the location calculator 430 and/or endoscope position estimator 420 can implement a filtering stage 535 to adjust one or both of the instrument and model positions based on the identified frequency of the respiration in order to compensate for the cyclic movement of the luminal network. Various implementations of the filtering stage 535 are described in more detail with respect to FIG. 6A-6C.

At block 530, the state estimator 440 can output an indication of the instrument position. The output can be provided to a navigation system, for example the surgical robotic system 110, to a user interface, for example display 202, or both. In some embodiments, the indication can be output to the state estimator 440 for use in determining a probable state of the instrument.

Figure 6A:
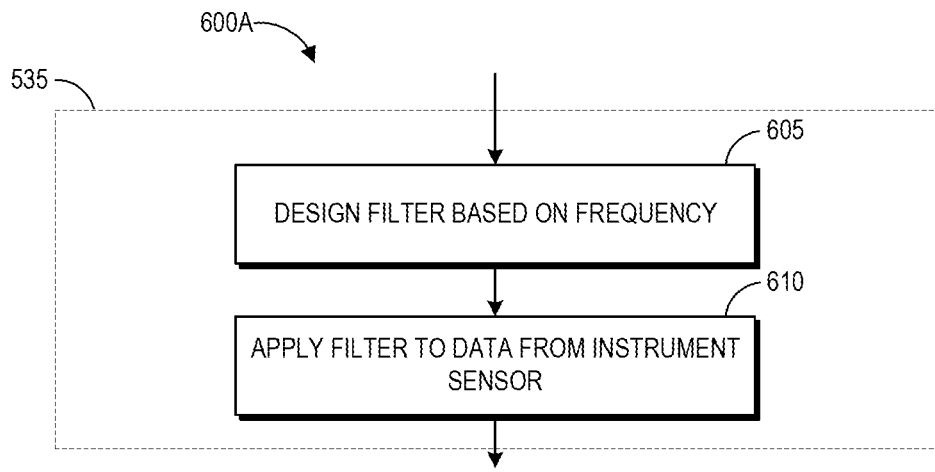
FIGS. 6A-6C depict flowcharts of various example processes that can be used for the adjustment block of FIG. 5.
Figure 6B:
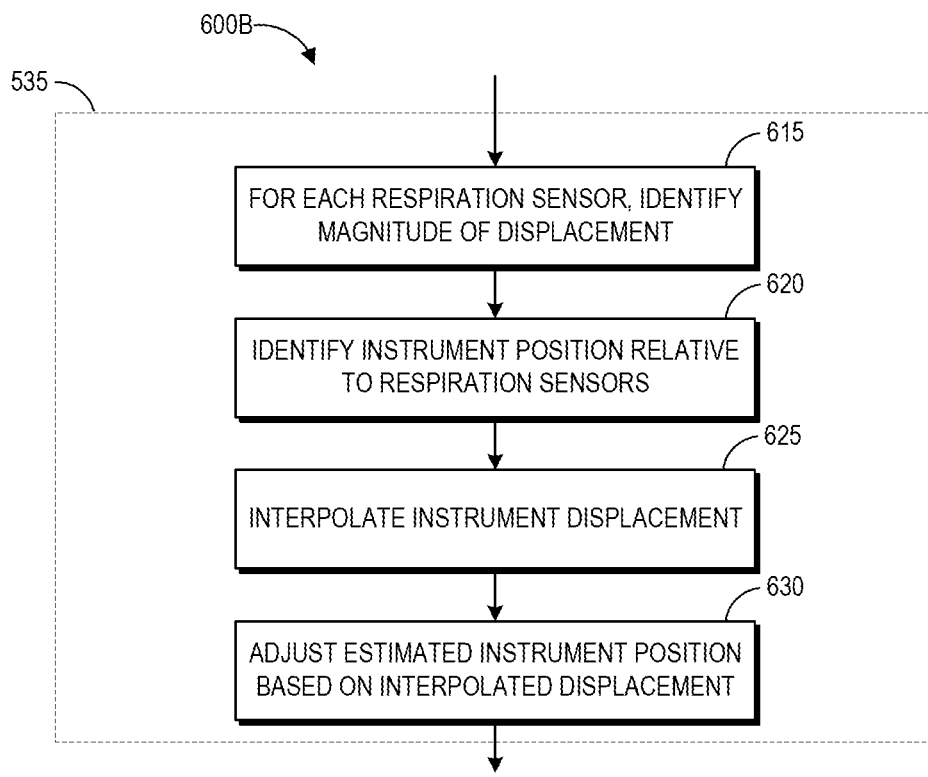
Figure 6C:
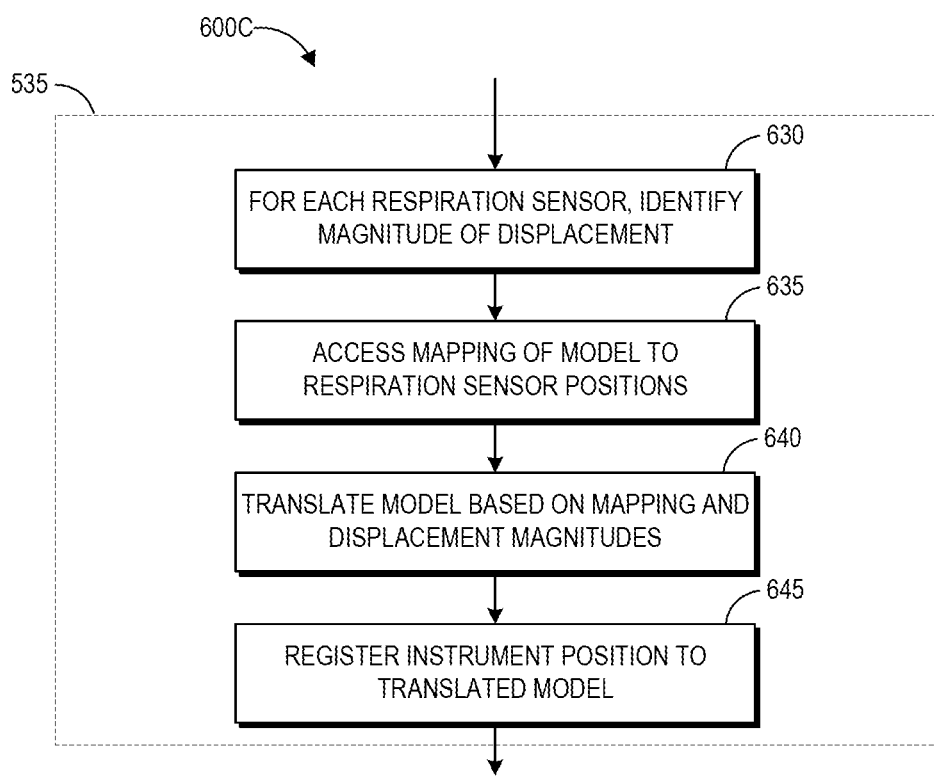

FIGS. 6A-6C depict flowcharts of various example processes that can be used for the filtering stage 535 of FIG. 5. The processes of FIGS. 6A-6C can be implemented by the navigation fusion system 400 FIG. 4, the control and sensor electronics 184 of FIG. 1, and/or the console base 201 of FIG. 2, or component(s) thereof.

Turning to FIG. 6A, depicted is one example process 600A that can be used for the filtering stage 535. At block 605, the endoscope position estimator 420 can design a filter based on the identified respiration frequency. As described above, in some embodiments the model of the patient's airways can be generated during breath-hold conditions. As such, the filter can be a band-pass or band-stop filter designed to select data from the instrument EM sensor during peak inspiration conditions corresponding to the breath-hold conditions during which the model was generated.

At block 610, the endoscope position estimator 420 can apply the filter designed at block 605 to the data from the instrument EM sensor to filter out portions of the data. By doing so, the process 600A can filter out portions of the EM sensor signal that are typically considered "noise" and that lead to inaccurate registrations with the 3D model. Because the EM sensor position is registered to a static 3D model, filtering out portions of the signal that occur during respiration conditions that vary from the respiration conditions during which the model was generated can increase the accuracy of the registration.

Turning to FIG. 6B, depicted is another example process 600B that can be used for the filtering stage 535. At block 615, the respiration frequency and/or phase identifier 410 can identify a magnitude of displacement of each respiration sensor. The magnitude can be measured relative to a "baseline" position of each sensor. The baseline can be set when calibrating the model coordinates to the EM field coordinates by recording the position of each sensor at the calibration time. In embodiments having multiple EM sensors positioned on the chest of a patient, a sensor attached closer to the sternum will show a lower magnitude of displacement than a sensor attached closer to the lower bounds of the lung.

At block 620, the endoscope position estimator 420 can identify a relative position of the instrument sensor relative to the respiration sensors. For example, x and y coordinates (representing the length and width locations in the EM field) can be compared to determine a closest respiration sensor and/or a relative distance between the instrument sensor and each respiration sensor.

At block 625, the process endoscope position estimator 420 can interpolate a displacement of the instrument sensor based on the displacements of the respiration sensors and the relative positioning of the instrument sensor and respiration sensors.

At block 630, the endoscope position estimator 420 can adjust the estimated instrument position calculated at block 515 by the interpolated displacement. As such, the adjusted position can represent a more accurate location of the instrument within the model by compensating for the displacement of the airway relative to the model coordinate frame.

Turning to FIG. 6C, depicted is another example process 600C that can be used for the filtering stage 535. At block 630, the respiration frequency and/or phase identifier 410 can identify a magnitude of displacement of each respiration sensor. This can be performed similarly to block 615 of process 600B described above.

At block 635, the location calculator 430 can access a mapping of the 3D model to respiration sensor positions. For example, each respiration sensor can be mapped to an x and y coordinate within the model.

At block 640, the location calculator 430 can translate the model to new coordinates within the EM field coordinate frame based on this mapping and the displacement magnitudes. For example, at each (x,y) coordinate to which a sensor was mapped, the process 600C can adjust the z-value of the (x,y,z) model coordinates based on the magnitude of displacement of the mapped sensor. For (x,y) coordinates between mapped sensors the z-value can be adjusted based on a magnitude interpolated based on the magnitudes and distances from adjacent sensors. As such, the position of the model within the EM field coordinate frame can be dynamically adjusted to reflect movement of the patient's airways.

At block 645, the location calculator 430 can register the instrument position to the translated model. For example, the location calculator 430 can access the (x,y,z) coordinate data of the instrument sensor within the EM field and identify a corresponding location within the translated model.

Some embodiments of the process 500 can use one or more of the processes 600A, 600B, 600C to calculate the instrument position relative to the model in the filtering stage 535.

Figure 7:
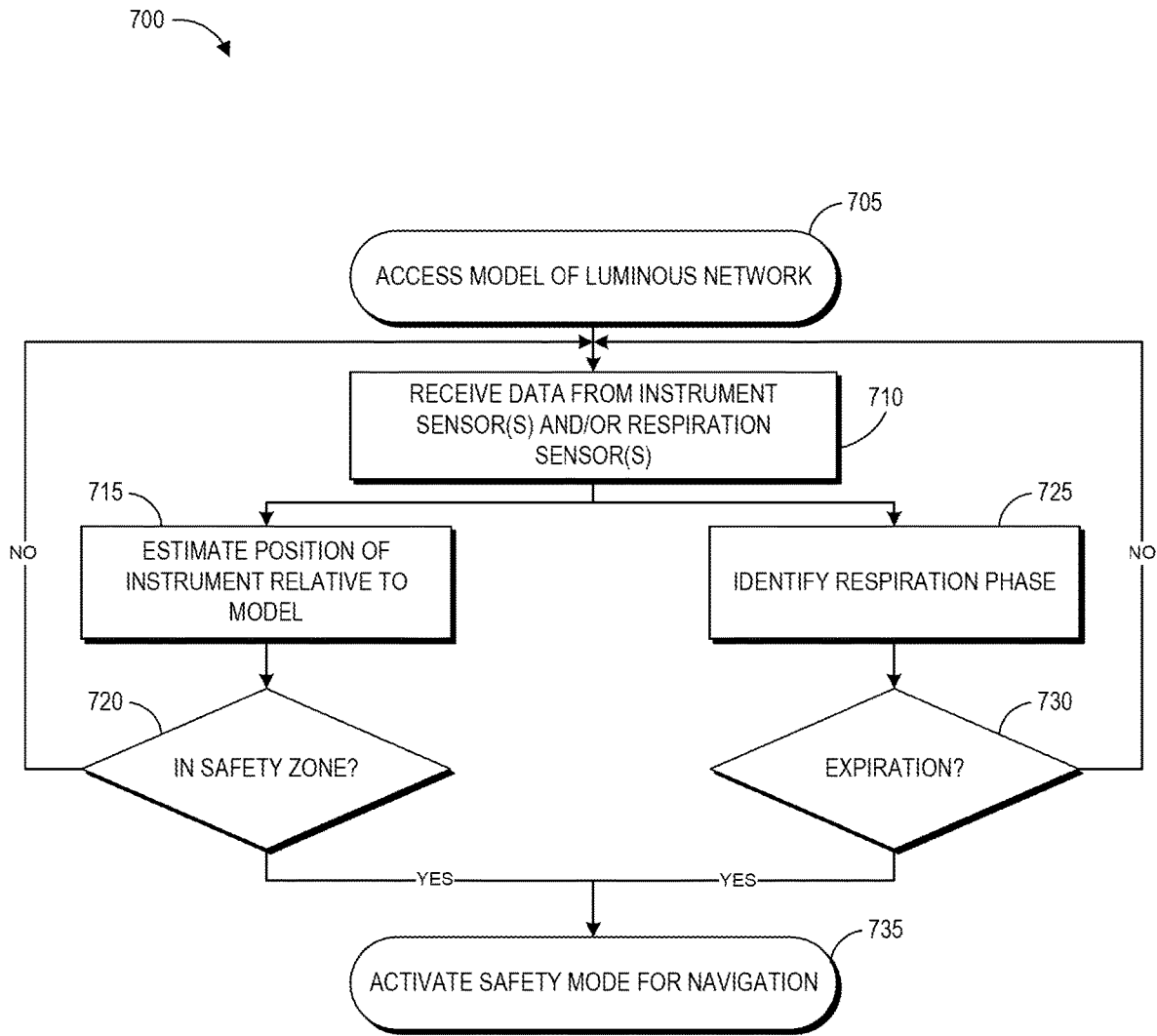
FIG. 7 depicts a flowchart of an example process for activating a safety mode during luminal network navigation as described herein.

In accordance with one or more aspects of the present disclosure, FIG. 7 depicts a flowchart of an example process 700 for activating a safety mode during luminal network navigation as described herein. The process 700 can be implemented by the navigation fusion system 400 FIG. 4, the control and sensor electronics 184 of FIG. 1, and/or the console base 201 of FIG. 2, or component(s) thereof.

At block 705, the state estimator 440 can access a 3D model of a patient's luminal network, for example from model data repository 425.

At block 710, the state estimator 440 can receive data from one or both of instrument sensor(s) and respiration sensor(s), for example from respiration sensor data repository 405 and endoscope EM sensor data repository 415, or can receive analyses of such data from modules 410, 420, and/or 430. As described above, the endoscope sensor data can provide location and/or orientation of a distal end of the endoscope within an EM field generated around the luminal network, and the respiration sensor data can be generated by a sensor positioned to detect movement of the luminal network. After block 710, the process 700 may split into two sub-processes that can be performed individually or together in order to determine whether to activate a safety mode. These sub-processes, if performed together, can be performed in parallel or in series.

If the state estimator 440 receives instrument sensor position data at block 710, then the process 700 can transition to block 715. At block 715, the state estimator 440 can estimate the position of the instrument relative to the model. This estimate can be performed by any of processes 600A-600C described above in some embodiments in order to compensate for cyclic motion.

At decision block 720, the safety mode controller 450 determines whether the position of the instrument falls within a predefined safety zone of the 3D model. As described above, safety zones can be predefined based on airway and instrument diameter comparisons. If the position of the instrument does not fall within a safety zone, the process 700 loops back to block 710 to receive new data from the sensors. In other embodiments, the process 700 can transition to block 725.

If the position of the instrument does fall within a safety zone, the process 700 transitions to block 735 and safety mode controller 450 activates a safety mode for further navigation (e.g., a next movement of the instrument or subsequent movement(s) of the instrument).

Turning to block 725, if the process 700 receives respiration sensor position data at block 710, then the process 700 can transition to block 725. At block 725 the respiration frequency and/or phase identifier 410 can identify the respiration phase as either inspiration or expiration.

At decision block 730, the safety mode controller 450 determines whether the phase of the respiration corresponds with predefined safety conditions. In some embodiments, all expiration phases can be identified as safety conditions. In some embodiments, expiration when in certain branches of the airways can correspond to the safety conditions. In some embodiments, the safety mode controller 450 can analyze historical respiration frequency data to predict whether the next movements of the instrument will fall within a respiration phase correlated with safety conditions. If the phase (or predicted phase) of the respiration does not correspond with predefined safety conditions, the process 700 loops back to block 710 to receive new data from the sensors. In other embodiments, the process 700 can transition to block 715.

If the phase (or predicted phase) of the respiration does correspond with predefined safety conditions, the process 700 transitions to block 735 and the safety mode controller 450 activates a safety mode for further navigation (e.g., a next movement of the instrument or all subsequent movement of the instrument).

If the process 700 transitions to block 735 because the position of the instrument has entered a safety zone, in some embodiments safety mode may be activated for all further insertion as airways tend to decrease in diameter further toward the lung periphery and navigation paths tend to travel from the central airways outward toward the periphery. If the process 700 transitions to block 735 because the phase of respiration (e.g., expiration) causes the process to activate safety mode, the safety mode may be activated for the duration of a predicted expiration cycle or until a next detected inspiration cycle.

In a safety mode, some embodiments of the process 700 may implement the navigation controller 460 to place limitations on instrument movement. For example, in safety mode the navigation controller 460 may prevent the surgical robotic system 110 from actuating instrument drivers. In such embodiments, navigation controller 460 can override a user input into a robotic system to guide insertion of the instrument while the safety mode is activated, for example during patient expiration.

In some embodiments, the safety mode controller 450 may determine that the airway diameter of airways positioned down the navigation path from the calculated instrument location are smaller than the diameter of the instrument. Thus, in the safety mode navigation controller 460 may prevent further insertion and the user may be prompted to insert a smaller, steerable channel through the working channel of the endoscope for any further navigation.

In a safety mode, some embodiments of the process 700 may not place limitations on instrument movement but instead may provide output to the user to indicate that caution should be exercised during instrument movement. Such outputs include graphical (e.g., on display), audible, or tactile (e.g., haptic feedback through an input device 204) warnings.

Overview of Example Navigation User Interfaces

Figure 8A:
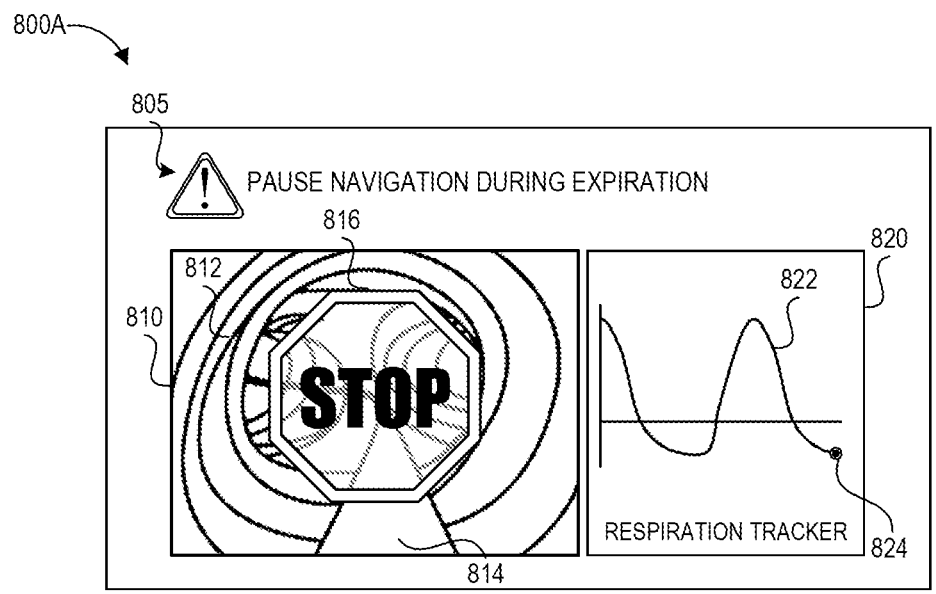
FIGS. 8A and 8B illustrate example user interfaces that can be presented to users during luminal network navigation in a safety mode as described herein.
Figure 8B:
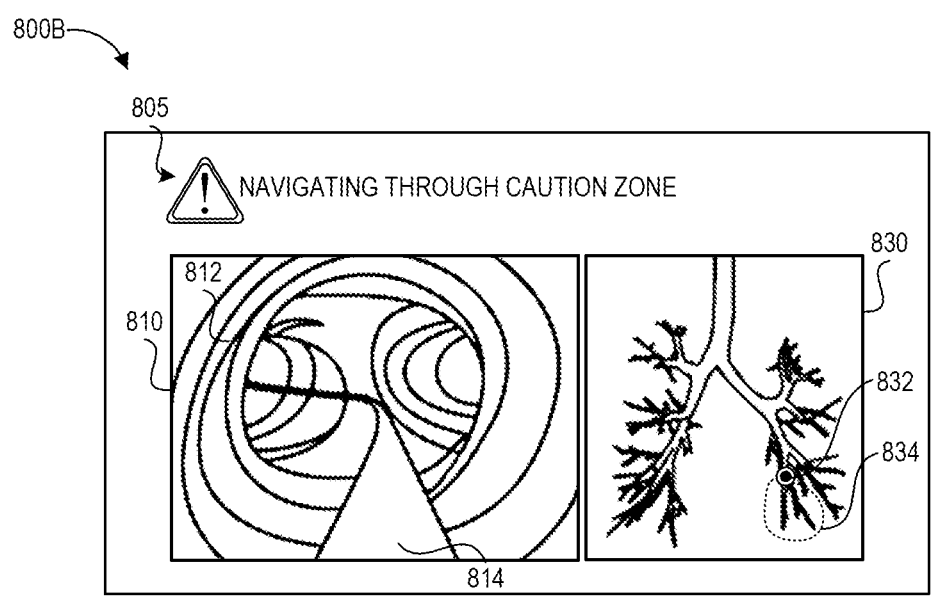

FIGS. 8A and 8B illustrate example user interfaces 800A, 800B that can be presented to users during luminal network navigation in a safety mode as described herein. For example, the user interfaces 800A, 800B can be presented on the display 202 of FIG. 2 in some embodiments.

FIG. 8A illustrates an example user interface 800A that can be presented to a user during the expiration phase of patient respiration. The example user interface 800 includes a warning 805, a virtual navigation section 810, and a respiration tracking section 820.

The virtual navigation section 810 includes a visualization of the patient airways 812 and a visualization of the navigation path 814 through the airways. As described above, this can be based on a 3D model in some embodiments. In some embodiments the virtual navigation section 810 can alternatively or additionally display images received from the endoscope camera.

The respiration tracking section 820 includes a waveform 822 of patient respiration and a marker 824 indicating the current point in the respiration cycle. In the waveform 822, portions of the waveform having positive slopes may represent inspiration and portions having negative slopes may represent expiration. Some embodiments may additionally display a predicted waveform of future respiration based, for example, on frequency analysis of previous respiration cycles and/or ventilator cycle data. As illustrated, the current point in the respiration cycle corresponds to an expiration phase.

The warning 805 alerts the operator of the system to pause navigation during expiration. In some embodiments, the warning 805 can be accompanied by an additional warning 816 overlaid onto the virtual navigation section 810. In other embodiments the color of the display may change, an alarm may sound, an input joystick may vibrate, or other visual, audible, or tactile indications can be presented to alert the user that the device is operating in safety mode. In some embodiments user control of the robotic system 110 can be overridden in this state in order to mitigate trauma to patient airways.

Turning to FIG. 8B, illustrated is another example user interface 800B that can be presented to a user during the navigation through a predetermined safety zone as described above. The user interface 800B includes a warning 805, a virtual navigation section 810, and a model display section 830.

As described above, the virtual navigation section 810 includes a visualization of the patient airways 812 and a visualization of the navigation path 814 through the airways.

The model display section 830 includes a graphical representation of the 3D model with a current position marker 832 and safety zone marker 834. As illustrated, the current position 832 is within the safety zone 834. As such, the warning 805 alerts the operator of the system that they are navigating through a caution zone. Further alerts can be provided to assist the user with pausing navigation during expiration in the zone.

Alternative Filter Techniques

As mentioned above, some embodiments may utilize an approach that: (a) receives raw sensor data for a given time period, (b) applies a function (e.g., Fourier Transform) to determine the respiration rate on the raw sensor data to determine the respiration rate for the given time period, and (c) applies a filter on the raw sensor data to remove the components of the raw sensor data attributable to the determined respiration rate. However, these approaches may introduce undesirable delay from (a)-(c). To lessen the delay from (a)-(c), some embodiments may utilize predictive techniques for predicting the respiration rate for a future time period. One predictive approach may involve using a non-linear Kalman filter (such as, an extended Kalman filter (EKF), unscented Kalman filter (UKF) or other suitable approaches that apply a Kalman filter to non-linear function) to predict respiration motion in near or substantially real-time. As used herein, "real-time" refers to processing applied immediately following acquisition of sensor data, for example processing on sensor data that is completed within a sufficiently short window of time such that the processed data is able to be used for navigation of the instrument. An EKF or multiple EKFs (one for patch, one for scope) can identify in real time the amplitude, direction and phase of respiration. Embodiments may remove the respiration motion detected by the EKF or EKFs from the raw EM sensor data generated by the EM sensors, or any other location sensor. The EKF may process historical raw sensor data to predict the respiration motion for a current time period. The predicted respiration motion is then used to filter out the respiration component in the raw sensor data. An EKF or multiple EKFs (one for patch, one for scope) can identify in real time the amplitude, direction and phase of respiration. Other example embodiments may use other predictive techniques, such as alpha-beta filtering, Bayesian filtering, particle filtering, or the like.

Compensation for Robotic Commands

In some embodiments, movement of the instrument may exhibit motions similar to respiration. To compensate for these motions, embodiment for detecting and compensation for respiration rate (or any other physiological induced motion) may use the commanded motion data used to control (e.g., insert, retract, articulate) the instrument to avoid detecting that motion as the respiration rate. For example, if the instrument's movement is at a given rate (as determinable by the commanded data), embodiments described above may apply a filter to the sensor data to remove data attributable to that movement.

Alternative Sensor Types

As described above, aside from using EM sensors to determine the location of the instrument, other embodiments may use other suitable sensor types. Such location sensors may include shape sensing fibers, accelerometers, vision detection algorithms, gyroscopes, or any other suitable sensor that can detect properties of motion.

Compensation for Other Physiological Noise

Although much of the embodiments described herein are detect and compensate for noise create from a patient's respiration rate, other embodiments may detect and compensate for noise created by other physiological properties of the patient, such as heart rate or any other detectable property. In such cases, where the heart rate may create noise in the EM data, these embodiments may detect the frequency of the heart rate and use the techniques discussed above to remove the noise created by the heart rate. Other noise artifacts may also be detected, as may occur if the patient experiences a periodic tremor or physical movement.

Implementing Systems and Terminology

Implementations disclosed herein provide systems, methods and apparatus for improved navigation of luminal networks.

It should be noted that the terms "couple," "coupling," "coupled" or other variations of the word couple as used herein may indicate either an indirect connection or a direct connection. For example, if a first component is "coupled" to a second component, the first component may be either indirectly connected to the second component via another component or directly connected to the second component.

The robotic motion actuation functions described herein may be stored as one or more instructions on a processor-readable or computer-readable medium. The term "computer-readable medium" refers to any available medium that can be accessed by a computer or processor. By way of example, and not limitation, such a medium may comprise RAM, ROM, EEPROM, flash memory, CD-ROM or other optical disk storage, magnetic disk storage or other magnetic storage devices, or any other medium that can be used to store desired program code in the form of instructions or data structures and that can be accessed by a computer. It should be noted that a computer-readable medium may be tangible and non-transitory. As used herein, the term "code" may refer to software, instructions, code or data that is/are executable by a computing device or processor.

The methods disclosed herein comprise one or more steps or actions for achieving the described method. The method steps and/or actions may be interchanged with one another without departing from the scope of the claims. In other words, unless a specific order of steps or actions is required for proper operation of the method that is being described, the order and/or use of specific steps and/or actions may be modified without departing from the scope of the claims.

As used herein, the term "plurality" denotes two or more. For example, a plurality of components indicates two or more components. The term "determining" encompasses a wide variety of actions and, therefore, "determining" can include calculating, computing, processing, deriving, investigating, looking up (e.g., looking up in a table, a database or another data structure), ascertaining and the like. Also, "determining" can include receiving (e.g., receiving information), accessing (e.g., accessing data in a memory) and the like. Also, "determining" can include resolving, selecting, choosing, establishing and the like.

The phrase "based on" does not mean "based only on," unless expressly specified otherwise. In other words, the phrase "based on" describes both "based only on" and "based at least on."

The previous description of the disclosed implementations is provided to enable any person skilled in the art to make or use the present invention. Various modifications to these implementations will be readily apparent to those skilled in the art, and the generic principles defined herein may be applied to other implementations without departing from the scope of the invention. For example, it will be appreciated that one of ordinary skill in the art will be able to employ a number corresponding alternative and equivalent structural details, such as equivalent ways of fastening, mounting, coupling, or engaging tool components, equivalent mechanisms for producing particular actuation motions, and equivalent mechanisms for delivering electrical energy.

What is claimed is:

1. A method of navigating a luminal network of a patient, the method comprising:
generating an electromagnetic (EM) field;
accessing a preoperative model representative of the luminal network;
accessing a registration mapping between a coordinate frame of the EM field and a coordinate frame of the preoperative model;
receiving an EM data signal from a set of one or more EM sensors at a distal end of a steerable instrument within the EM field;
calculating a frequency of respiration of the patient based on a respiration data signal from a set of respiration sensors configured to be placed on the patient;
applying a predictive filter to the EM data signal and the respiration data signal, the predictive filter configured to predict respiration motion due to the respiration;
removing components of the EM data signal attributable to the predicted respiration motion;
calculating, based on the EM data signal with the components removed, at least one position of the set of EM sensors within the EM field;
determining a position of the distal end of the steerable instrument relative to the preoperative model via transforming the at least one position of the set of EM sensors within the EM field using the registration mapping;
determining at least one position of the set of EM sensors relative to the set of respiration sensors;
calculating at least one positional displacement of the set of EM sensors between inspiration and expiration phases of the respiration of the patient based on (i) the determined at least one position of the set of EM sensors relative to the set of respiration sensors and (ii) at least one magnitude of displacement of the set of respiration sensors between the inspiration and expiration phases; and
determining a position of the distal end of the steerable instrument relative to the preoperative model based on the calculated at least one positional displacement of the set of EM sensors between the inspiration and expiration phases.

2. The method of claim 1, further comprising:
transforming one or more data signals from the set of respiration sensors into a frequency domain representation of the one or more data signals; and
identifying the frequency of respiration from the frequency domain representation of the one or more data signals.

3. The method of claim 1, wherein the set of respiration sensors comprises a first additional EM sensor positioned, in use, at a first position on a body surface of the patient and a second additional EM sensor positioned, in use, at a second position of the body surface, wherein the second position is spaced apart from the first position such that a first magnitude of displacement of the first additional EM sensor is greater than a second magnitude of displacement of the second additional EM sensor between the inspiration and expiration phases.

4. The method of claim 3, further comprising:
determining a relative positioning of the set of EM sensors with respect to the first and second additional EM sensors; and
interpolating between the first and second magnitudes of displacement based on the determined relative positioning of the set of EM sensors, wherein the calculation of the positional displacement of the set of EM sensors between the inspiration and the expiration phases is based on the interpolated magnitude.

5. The method of claim 3, further comprising:
estimating a movement vector for at least a portion of the preoperative model based on the at least one magnitude of displacement;
translating the preoperative model within the coordinate frame of the EM field based on the estimated movement vector; and
determining the position of the distal end of the steerable instrument based on the translated preoperative model.

6. The method of claim 5, wherein the translating the preoperative model within the coordinate frame of the EM field comprises:
moving a first portion of the preoperative model to first new coordinates based on the first magnitude of displacement; and
moving a second portion of the preoperative model to second new coordinates based on the second magnitude of displacement.

7. The method of claim 1, further comprising:
generating a graphical representation of the position of the distal end of the steerable instrument relative to the preoperative model; and
rendering the generated graphical representation on a display.

8. A system configured to navigate a luminal network of a patient, the system comprising:
a field generator configured to generate an electromagnetic (EM) field;
a set of one or more EM sensors at a distal end of a steerable instrument;
a set of one or more respiration sensors configured to be placed on the patient;
at least one computer-readable memory having stored thereon executable instructions; and
one or more processors in communication with the at least one computer-readable memory and configured to execute the instructions to cause the system to at least:
access a preoperative model representative of the luminal network;
access a registration mapping between a coordinate frame of the EM field and a coordinate frame of the preoperative model;
receive an EM data signal from the set of EM sensors within the EM field;
calculate a frequency of respiration of the patient based on a respiration data signal from the set of respiration sensors;
according to a first process:
apply a predictive filter configured to predict respiration motion due to the respiration to the EM data signal and the respiration data signal;
remove components of the EM data signal attributable to the predicted respiration motion;
calculate, based on the EM data signal with the components removed, at least one position of the set of EM sensors within the EM field; and
determine a position of the distal end of the steerable instrument relative to the preoperative model via transforming the at least one position of the set of EM sensors within the EM field using the registration mapping; and according to a second process:
calculate at least one positional displacement of the set of EM sensors between inspiration and expiration phases of the respiration of the patient based on (i) at least one position of the set of EM sensors relative to the set of respiration sensors and (ii) at least one magnitude of displacement of the set of respiration sensors between the inspiration and expiration phases; and determine the position of the distal end of the steerable instrument relative to the preoperative model based on the calculated at least one positional displacement of the set of EM sensors between the inspiration and expiration phases.

9. The system of claim 8, wherein the one or more processors are configured to execute the instructions to cause the system to at least:
transform one or more data signals from the set of respiration sensors into a frequency domain representation of the one or more data signals; and
identify the frequency of respiration from the frequency domain representation of the one or more data signals.

10. The system of claim 8, wherein the set of respiration sensors comprises a first additional EM sensor positioned, in use, at a first position on a body surface of the patient and a second additional EM sensor positioned, in use, at a second position of the body surface, wherein the second position is spaced apart from the first position such that a first magnitude of displacement of the first additional EM sensor is greater than a second magnitude of displacement of the second additional EM sensor between the inspiration and expiration phases.

11. The system of claim 10, wherein the one or more processors are configured to execute the instructions to cause the system to at least:
determine a relative positioning of the set of EM sensors with respect to the first and second additional EM sensors; and
interpolate between the first and second magnitudes of displacement based on the determined relative positioning of the set of EM sensors, wherein the calculation of the positional displacement of the set of EM sensors between the inspiration and the expiration phases is based on the interpolated magnitude.

12. The system of claim 10, wherein the one or more processors are configured to execute the instructions to cause the system to at least:
estimate a movement vector for at least a portion of the preoperative model based on the at least one magnitude of displacement;
translate the preoperative model within the coordinate frame of the EM field based on the estimated movement vector; and
determine the position of the distal end of the steerable instrument based on the translated preoperative model.

13. The system of claim 12, wherein, to translate the preoperative model within the coordinate frame of the EM field, the one or more processors are configured to execute the instructions to cause the system to at least:
move a first portion of the preoperative model to first new coordinates based on the first magnitude of displacement; and move a second portion of the preoperative model to second new coordinates based on the second magnitude of displacement.

14. The system of claim 8, further comprising a display, wherein the one or more processors are configured to execute the instructions to cause the system to at least:
activate a safety mode for navigation based on one or more of the frequency of respiration or one or more safety zones; and
render information associated with the safety mode on the display.

15. A non-transitory computer readable storage medium having stored thereon instructions that, when executed, cause at least one computing device to at least:
receive a first data signal from an electromagnetic (EM) sensor on an instrument inserted, in use, in a tissue site of a patient within an EM field;
access a registration mapping between coordinate frames of the EM field and the tissue site;
receive a second data signal from at least one additional sensor configured to detect movement of the tissue site, the at least one additional sensor configured to be placed on the patient;
calculate, based on the first data signal, a position of the EM sensor within the EM field disposed around the tissue site;
calculate, based on the second data signal, a frequency of cyclic movement of the tissue site;
according to a first process;
apply a predictive filter configured to predict respiration motion due to respiration of the patient to the first data signal and the second data signal;
remove components of the first data signal attributable to the predicted respiration motion;
calculate, based on the first data signal with the components removed, a position of the EM sensor within the EM field; and
determine a position of the instrument relative to the tissue site via transforming the position of the EM sensor within the EM field using the registration mapping; and
according to a second process:
calculate a positional displacement of the EM sensor between inspiration and expiration phases of the respiration of the patient based on (i) a position of the EM sensor relative to the at least one additional sensor and (ii) at least one magnitude of displacement of the at least one additional sensor between the inspiration and expiration phases; and
determine the position of the instrument based on the calculated positional displacement of the EM sensor between the inspiration and expiration phases.

16. The non-transitory computer readable storage medium of claim 15, wherein the instructions, when executed, cause the at least one computing device to:
transform the second data signal from the at least one additional sensor into a frequency domain representation; and
identify the frequency of the cyclic movement from the frequency domain representation.

17. The non-transitory computer readable storage medium of claim 15, wherein the at least one additional sensor comprises a first additional EM sensor positioned, in use, at a first position on the patient and a second additional EM sensor positioned, in use, at a second position of the patient, wherein the second position is spaced apart from the first position such that a first magnitude of displacement of the first additional EM sensor is greater than a second magnitude of displacement of the second additional EM sensor between the inspiration and expiration phases, and wherein the instructions, when executed, cause the at least one computing device to:

determine a position of the EM sensor relative to the first and second additional EM sensors; and interpolate between the first and second magnitudes of displacement based on the determined position of the EM sensor relative to the first and second additional EM sensors, wherein the calculation of the positional displacement of the EM sensor between the inspiration and the expiration phases is based on the interpolated magnitude.

18. The non-transitory computer readable storage medium of claim 17, wherein the instructions, when executed, cause the at least one computing device to:

access data representing a model representing a topography of the tissue site, where the registration mapping is further between the coordinate frame of the EM field and a coordinate frame of the model, wherein determining the position of the instrument is based on the registration mapping, the frequency, and the position of the EM sensor within the EM field.

19. The non-transitory computer readable storage medium of claim 18, wherein the tissue site comprises respiratory airways, and wherein the instructions, when executed, cause the at least one computing device to:

estimate a movement vector for at least a portion of the model based on the at least one magnitude of displacement;

translate the model within the coordinate frame of the EM field based on the estimated movement vector; and determine the position of the instrument based on the translated model.

20. The non-transitory computer readable storage medium of claim 19, wherein, to translate the model within the coordinate frame, the instructions, when executed, cause the at least one computing device to:

move a first portion of the model to first new coordinates based on the first magnitude of displacement; and move a second portion of the model to second new coordinates based on the second magnitude of displacement.

* * * * *